US008960005B2

(12) United States Patent
Ruzzene et al.

(10) Patent No.: US 8,960,005 B2
(45) Date of Patent: Feb. 24, 2015

(54) FREQUENCY-STEERED ACOUSTIC TRANSDUCER (FSAT) USING A SPIRAL ARRAY

(71) Applicant: Georgia Tech Research Corporation, Atlanta, GA (US)

(72) Inventors: Massimo Ruzzene, Smyrna, GA (US); Matteo Senesi, Atlanta, GA (US); Buli Xu, West Columbia, SC (US)

(73) Assignee: Georgia Tech Research Corporation, Atlanta, GA (US)

( * ) Notice: Subject to any disclaimer, the term of this patent is extended or adjusted under 35 U.S.C. 154(b) by 80 days.

(21) Appl. No.: 13/712,461

(22) Filed: Dec. 12, 2012

(65) Prior Publication Data

US 2014/0157898 A1 Jun. 12, 2014

Related U.S. Application Data

(60) Provisional application No. 61/569,423, filed on Dec. 12, 2011.

(51) Int. Cl.
| | |
|---|---|
| *G01N 9/04* | (2006.01) |
| *G01N 29/12* | (2006.01) |
| *G01N 29/24* | (2006.01) |
| *G01N 29/26* | (2006.01) |
| *G01N 29/42* | (2006.01) |

(52) U.S. Cl.
CPC .............. *G01N 29/12* (2013.01); *G01N 29/245* (2013.01); *G01N 29/262* (2013.01); *G01N 29/42* (2013.01); *G01N 2291/0258* (2013.01); *G01N 2291/106* (2013.01)
USPC .................................. 73/596; 73/626; 73/628

(58) Field of Classification Search
USPC .............. 702/39, 159; 73/579, 296, 618, 620, 73/625–628, 633, 640, 645–648
See application file for complete search history.

(56) References Cited

U.S. PATENT DOCUMENTS

| | | | | |
|---|---|---|---|---|
| 4,213,344 A | * | 7/1980 | Rose ............................... | 73/620 |
| 5,511,550 A | * | 4/1996 | Finsterwald ................... | 600/459 |
| 5,550,792 A | * | 8/1996 | Crandall et al. ............... | 367/155 |
| 5,692,029 A | * | 11/1997 | Husseiny et al. ............... | 378/88 |
| 5,974,889 A | * | 11/1999 | Trantow ........................ | 73/624 |
| 5,987,991 A | * | 11/1999 | Trantow et al. ................ | 73/624 |

(Continued)

*Primary Examiner* — Peter Macchiarolo
*Assistant Examiner* — Samir M Shah
(74) *Attorney, Agent, or Firm* — Troutman Sanders LLP; Ryan A. Schneider; Benjamin C. Wiles

(57) ABSTRACT

Frequency-steerable acoustic transducers (FSATs) that allow directional generation or sensing of waves propagating in two-dimensional domains. Directionality is the result of the spatial filtering effect produced by the characteristic shape of the sensing surface. A wavenumber spiral FSAT (WS-FSAT) maps the direction of wave sensing in the [0°, 180°] range to a specific frequency component in the spectrum of the received signal. The use of a wavenumber spiral FSAT operating in sensing mode can be used for the localization of broadband acoustic events. One configuration includes a broadband source generating guided elastic waves in an isotropic plate. The WS-FSAT records the plate response and defines the source location through a time-frequency analysis of the received signal. The frequency selective response of the WS-FSAT directly maps the dominant component of the received signal to the direction of arrival of the incoming wave, thus greatly facilitating the source localization procedure.

1 Claim, 25 Drawing Sheets
(25 of 25 Drawing Sheet(s) Filed in Color)

(56) References Cited

U.S. PATENT DOCUMENTS

| | | | |
|---|---|---|---|
| 6,006,163 A * | 12/1999 | Lichtenwalner et al. | 702/36 |
| 6,279,397 B1 * | 8/2001 | Dwyer | 73/606 |
| 6,370,964 B1 * | 4/2002 | Chang et al. | 73/862.046 |
| 6,771,412 B2 * | 8/2004 | Torchigin | 359/305 |
| 6,996,480 B2 * | 2/2006 | Giurgiutiu et al. | 702/35 |
| 7,406,220 B1 * | 7/2008 | Christensen et al. | 385/27 |
| 7,414,577 B2 * | 8/2008 | Mohamadi | 342/372 |
| 7,417,706 B2 * | 8/2008 | Holmes | 349/202 |
| 7,428,842 B2 * | 9/2008 | Fair et al. | 73/626 |
| 7,836,768 B2 * | 11/2010 | Young et al. | 73/620 |
| 7,881,881 B2 * | 2/2011 | Giurgiutiu et al. | 702/39 |
| 7,917,311 B2 * | 3/2011 | Finkel et al. | 702/39 |
| 8,011,249 B2 * | 9/2011 | Junker et al. | 73/623 |
| 8,176,786 B2 * | 5/2012 | Sohn et al. | 73/602 |
| 8,286,490 B2 * | 10/2012 | Ruzzene et al. | 73/618 |
| 8,544,328 B2 * | 10/2013 | Sohn et al. | 73/598 |
| 8,707,787 B1 * | 4/2014 | Sohn et al. | 73/602 |
| 2006/0097942 A1 * | 5/2006 | Tanaka et al. | 343/770 |
| 2009/0301198 A1 * | 12/2009 | Sohn et al. | 73/598 |
| 2010/0206080 A1 * | 8/2010 | Ruzzene et al. | 73/618 |

* cited by examiner (a)

(b)

(a)

(b)

(a) 10 deg (b) 30 deg (c) 50 deg (d) 70 deg (e) 90 deg (f) 110 deg

FREQUENCY-STEERED ACOUSTIC TRANSDUCER (FSAT) USING A SPIRAL ARRAY

CROSS-REFERENCE TO RELATED APPLICATIONS

This application claims the benefit of U.S. Provisional Application No. 61/569,423 filed 12 Dec. 2011, the entire contents and substance of which are hereby incorporated by reference.

STATEMENT REGARDING FEDERALLY SPONSORED RESEARCH OR DEVELOPMENT

This invention was made with Government support under Agreement/Contract Number CMMI-0800263, awarded by the National Science Foundation. The Government has certain rights in the invention.

BACKGROUND OF THE INVENTION

1. Field of Invention

This invention relates generally to structural health monitoring and non-destructive evaluation, and more specifically to spiral-shaped arrays used as effective ways to direct energy without the need for individual control of the array components.

2. Background and Related Art

Structural health monitoring (SHM) is essential to prevent failure in a number of aerospace components, civil infrastructures, and mechanical systems. Research in this field is playing a key role in improving safety and reducing maintenance costs. The use of guided waves (GWs) has recently attracted great interest because of their potential to perform long-range and fast inspection, in contrast with conventionally employed normal beam ultrasonic scanning, which is local, and hence time-consuming. However, effective interrogation of remote areas of a structure using GWs requires suitable techniques for a correct localization of damages or anomalous acoustic sources such as impacts or leaks.

Multiple transducers are typically employed for this purpose, which are often arranged in array configurations. This allows for beam steering at selected directions, but comes at the cost of significant hardware complexity needed to individually control large numbers of elements, and/or intensive signal processing required for the implementation of processes such as delay-and-sum. Drastic hardware simplification and cost reduction of GW-based SHM could be achieved by using transducers with inherent directional capabilities. This involves designing the transducer shape or the arrangement of the sensing material so that it exhibits preferential radiation/sensing directions. Examples of devices with inherent beam steering capabilities include the CLoVER transducer as well as rosette configurations of macro-fiber composite (MFC) devices.

Guided wave methods have been proposed for SHM of plate-like structures using permanently attached piezoelectric transducers, which generate and sense waves to evaluate the presence of damage. Effective interrogation of structural health is often facilitated by sensors and actuators with the ability to perform directional scanning. This enhances the sensitivity of the inspection and simplifies the determination of the damage location.

Wave steering through phased arrays is a well-established technique, used extensively in ultrasonic imaging for medical and nondestructive evaluation (NDE) applications. Recent research has investigated the application of guided wave-based phased arrays for SHM. One conventional method implements a phased comb transducer array using hardware and software delay-and-sum beamforming algorithms on pipes.

In another, a virtual beam steering concept named EUSR using permanently attached lead zirconate titanate (PZT) transducer arrays. Another presents a circular array integrated with a deconvolution algorithm to improve imaging quality. Others have explored the optimization of linear arrays and presented a two-dimensional (2D) square array capable of virtual beam steering in a 360° range. Others have compared phased-array beamforming results using monolithic PZT and MFC transducers and concluded the latter have better directivity at certain steering angles.

Still other researchers propose the use of spatially distributed arrays, comprising sensors distributed over a large area, as an effective approach to image damage inside and outside the area enclosed by the array. In this regard, algorithms have been proposed that apply delay-and-sum procedures to each pixel of the image, so that waves can be considered as steered to each pixel point.

All these promising results not only demonstrate the potential benefits of beam steering for guided waves generation and sensing, but also underline some limitations. One such limitation is inherent in the array basic principle of operation, i.e., the delay-and-sum algorithm, which requires wiring and multiplexing of individual array elements.

In fact, most ultrasonic phased array technologies require electronic beam steering devices and corresponding hardware complexity, which makes their implementation as embedded devices problematic. For this reason, there is growing interest in the development of sensors and actuators with inherent directional and beam steering properties, so that cost and hardware limitations of traditional phased arrays can be partially overcome.

One such attempt is guided wave steering by firing in sequence multiple sections of wedge-shaped anisotropic piezo-composite transducers arranged in a circular ring pattern. Another configuration includes a two-dimensional (2D) periodic array of piezoelectric discs featuring frequency-dependent directivity in virtue of the interference phenomena associated with the spatial arrangement of the array elements. All elements of the array are fired simultaneously, so that the control hardware is reduced to a single channel, and beam steering is achieved through a sweep of the excitation frequency. In addition, the spatial arrangement of the array components is such that radiation is achieved at specific wavenumbers, so that it can be tuned to a specific wave mode.

To overcome the operability, efficiency and cost issues mentioned above, an improved structural health monitoring and non-destructive evaluation system is highly desirable. It is the intention of the present invention to provide for such industrial needs.

BRIEF SUMMARY OF THE INVENTION

Briefly described, in a preferred form, the present invention comprises a system, method, and apparatus providing frequency steerable acoustic transducers using a spiral array.

The directional transducer of the present invention exploits the frequency-based beam steering concept. In the frequency steering approach, directional generation/sensing of GWs is achieved through a spatial filtering effect produced by the simultaneous activation of multiple array nodes arranged in a specific geometrical configuration. As the spatial filtering is frequency-dependent, a direct relationship can be established between the direction of propagation and the spectral content of the transmitted/received signal.

The present invention was initially implemented through a periodic FSAT with elements all connected in parallel, which result in a single-channel device allowing for beam steering in four preferential directions. Arbitrary directional scanning within the [0°, 180°] angular range subsequently demonstrated through an extension of the FSAT design led to a spiral-shaped FSAT.

The spiral denomination of this development of FSAT refers to the spiral configuration of the wavenumber representation of the transducer shape, and not to its shape in the physical domain. For this reason, the present inventive configuration represents a departure from spiral-shaped transducers previously proposed in the literature for antenna, strain measurement, and other SHM applications, among others.

The present invention comprises fabrication and experimental validation of prototype wavenumber spiral FSATs (WS-FSATs) realized by photolithography-based electrode patterning on a Polyvinylidene Fluoride (PVDF) substrate. This flexible piezoelectric material is being increasingly used for GW generation and sensing, and allows for complex transducer geometry design. The fabricated FSAT is characterized and proposed for sensing operation. Ad-hoc signal processing algorithms are applied for broadband source localization.

Further, a new sensor geometry overcoming the limited angular resolution is presented. Specifically, a new design with improved frequency-steerable capabilities, while still keeping minimal hardware requirements, is shown. A theoretical approach is developed to define the directivity of an arbitrary shaped transducer. A spiral array design with directional capabilities continuously varying through frequency sweep is then proposed. The plate response and its directionality at various frequencies are evaluated first numerically. A virtual approach using a laser vibrometer has been developed to perform a preliminary experimental validation of its capabilities. The agreement between numerical predictions and experimental results demonstrate the feasibility of the proposed approach for directional actuation and sensing of guided waves in plate structures.

The present FSAT geometry provides spatial filtering and hence directional sensing, is easy and inexpensive to fabricate based on inkjet printing, provides accurate localization of acoustic sources using one channel, provides chirp illumination and signal processing allow for scatterer imaging, and has low hardware and software complexity that can enable in-situ and wireless SHM.

These and other objects, features and advantages of the present invention will become more apparent upon reading the following specification in conjunction with the accompanying drawing figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various features and advantages of the present invention may be more readily understood with reference to the following detailed description taken in conjunction with the accompanying drawings, wherein like reference numerals designate like structural elements, and in which.

DETAILED DESCRIPTION OF THE INVENTION

Figure 1:
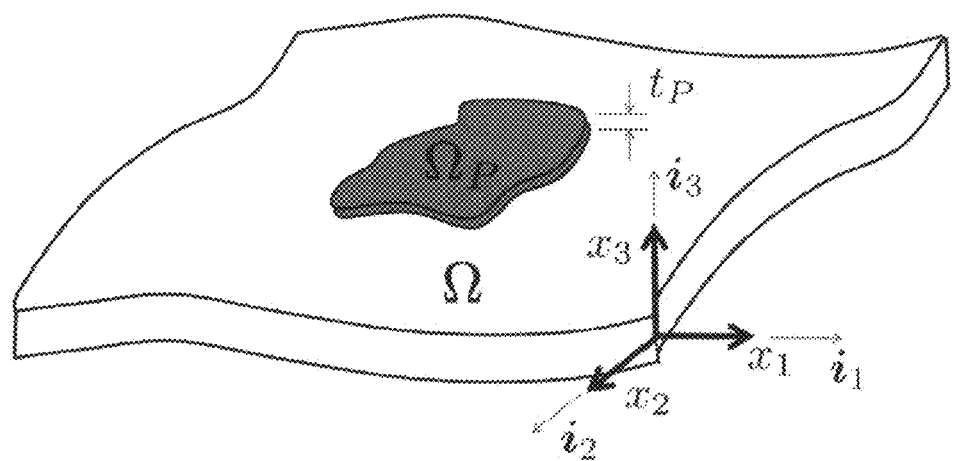
FIG. 1: Plate with arbitrarily shaped piezoelectric sensor bonded on the top surface, and considered coordinate system.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

Array systems and related methods for structural health monitoring are provided, several exemplary embodiments of which will be described in detail. In some embodiments, beam steering of energy propagated from an array is achieved by exploiting interference phenomena (i.e., constructive and/or destructive interference) generated by spatial periodicity of the array and the simultaneous activation of its components. Such interference phenomena produce waves with frequency dependent directional characteristics, which allow directional scanning to be performed simply through a frequency sweep. As such, the need for beam-forming algorithms and associated hardware may be avoided. In addition, spatially periodic piezoelectric actuators used in some embodiments can be exploited for tuning the excitation to a specific wave mode and, therefore, may be able to combine mode tuning with beam steering capabilities in a single device.

Formulation of Piezoelectric Sensing for Lamb Waves

The equations that govern sensing of elastic waves (Lamb waves) through surface mounted piezoelectric patches are herein presented. The case of a piezo patch of arbitrary shape is illustrated as a general framework for the subsequent illustration of the principles of directional sensing through properly shaped patches. Even if the formulation considers the sensing mode, the actuation mode of the transducer is straightforward.

Plate Configuration and Piezoelectric Constitutive Relations

The system under consideration is illustrated in FIG. 1. The domain of interest comprises a mechanical structure (thin plate) on an open domain $\Omega$ and of a piezoelectric domain $\Omega_p$ of thickness $t_p$. The reference system used for the analysis is located at the mid-surface of the structure, with coordinates $x_1$, $x_2$ defining the plane of the structure.

The constitutive equations for the piezoelectric domain are expressed as:

$$s = C^E e - e^T E$$

$$D = ee + e^\epsilon E \qquad (1)$$

where $s = \{\sigma_{11}\ \sigma_{22}\ \sigma_{33}\ \tau_{13}\ \tau_{23}\ \tau_{12}\}^T$ and $e = \{\epsilon_{11}\ \epsilon_{22}\ \epsilon_{33}\ \gamma_{13}\ \gamma_{23}\ \gamma_{12}\}^T$ respectively are the mechanical stress and strain vectors, $D = \{D_1\ D_2\ D_3\}^T$ is the electric charge vector, and $E = \{E_1\ E_2\ E_3\}^T$ is the electric field vector. Also, CT is the stiffness matrix of the material at constant electric field, e is the piezoelectric coupling matrix evaluated at constant stress, while $e^\epsilon$ denotes the permittivity matrix at constant strain. Equation (1) holds over the domain of the structure covered by the piezoelectric patch, defined by $x \in \Omega_p$, where $x = x_1 i_1 + x_2 i_2$ denotes a position vector on the plane of the structure.

It is here convenient to extend the validity of the piezoelectric constitutive relation to the entire domain of analysis $\Omega$ by introducing a functional $\phi(x)$ defined as:

$$\varphi(x) = \begin{cases} 1, & x \in \Omega_P \\ 0, & x \in \Omega - \Omega_P \end{cases} \qquad (2)$$

which describes the shape of the patch. A second function $\psi(x)$ is introduced to allow for different polarizations to be present within the piezoelectric domain. For simplicity, and in light of practicality, the case of alternating polarizations over specified sub-regions of $\Omega_p$ is considered, so that the function $\psi(x) = \pm 1$, $x \in \Omega_p$ depending on the polarization distribution.

Accordingly, equation (1) can be rewritten as:

$$\left\{\begin{array}{c}s\\D\end{array}\right\} = \varphi(x)\begin{bmatrix}C^E & -\psi(x)e^T\\\psi(x)e & e^\varepsilon\end{bmatrix}\left\{\begin{array}{c}e\\E\end{array}\right\}, x \in \Omega \quad (3)$$

For operation of the patch in a sensing mode, the second of equations (3) is of particular importance and will be analyzed in detail. The analysis is simplified by introducing a number of assumptions which reduce the size of the problem. First, it is assumed that the piezoelectric material is polarized along its thickness direction $x_3$, so that two of the components of the electric displacement vector are zero ($D_1=D_2=0$). The sensor is also considered thin, therefore $\sigma_{33} \approx 0$, and in a state of plane strain, i.e. $\epsilon_{33} \approx \gamma_{13} \approx \gamma_{23} \approx 0$, and $e = \{\epsilon_{11}\ \epsilon_{22}\ \gamma_{12}\}^T$.

The second of equations (3) reduces to:

$$D_3 = \phi(x)b^T D = \phi(x)b^T(\psi(x)ee + e^\varepsilon E), x \in \Omega \quad (4)$$

where $b = [0, 0, 1]^T$. Considering the strain-charge form of the piezoelectric constitutive equations, equation (4) can be rewritten as follows:

$$D_3 = \phi(x)b^T[\psi(x)d^\sigma C^E e + (e^\sigma - d^\sigma C^E d^{\sigma^T})EJ, x \in \Omega \quad (5)$$

where $d^\sigma$, $e^\sigma$ respectively denote the matrix of the piezoelectric strain constants and of the permittivity constants evaluated at constant stress.

Voltage Generated by Piezo Sensors of Arbitrary Shape

In sensing mode, the total charge developed over the piezoelectric area is $\int_{\Omega_P} D_3 dx = \int_\Omega \phi(x) D_3 dx \approx 0$. Integration of both sides of equation (5) therefore gives:

$$b^T d^\sigma C^E \int_\Omega e\phi(x)\psi(x)dx = b^T(d^\sigma C^E d^{\sigma^T} - e^\sigma)\int_\Omega \phi(x)Edx \quad (6)$$

where it was assumed that all properties of the piezoelectric patch are constant over its area $\Omega_P$. Equation (6) can be simplified by imposing that $E_1 = E_2 = 0$, and that the voltage varies linearly across the thickness of the piezo $t_P$ which gives:

$$E_3 = \frac{V}{t_P} \quad (7)$$

where V is the total voltage measured at the electrodes of the piezos. Accordingly, in equation (6), the electric field vector can be expressed as:

$$E = \frac{V}{t_P}b \quad (8)$$

Substituting in equation (6), and solving for the measured voltage V gives:

$$V = \frac{t_P}{A_P[b^T(d^\sigma C^E d^{\sigma^T} - e^\sigma)b]} b^T d^\sigma C^E \int_\Omega ef(x)dx \quad (9)$$

where $A_P = \int_\Omega \phi(x)dx$ is the area occupied by the piezoelectric patch, and where $f(x) = \phi(x)\psi(x)$ is introduced to simplify the notation.

Figure 2:
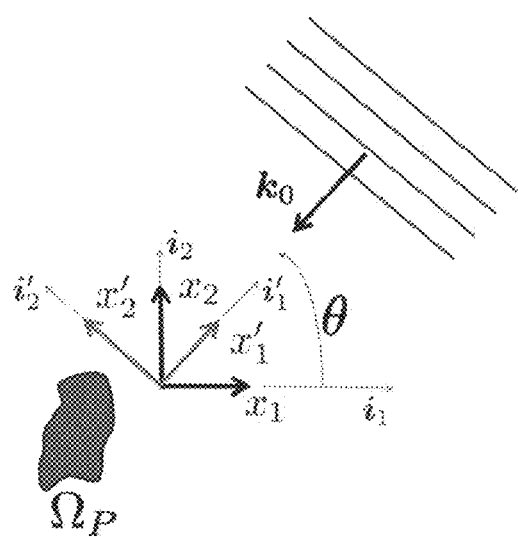
FIG. 2: Schematic of plane wave propagating at angle θ on the plane of the structure x.

The sensing voltage expressed in equation (9) can be evaluated in the presence of a plane wave propagating in the plane of the structure at frequency $\omega$. The surface displacement can be in general be expressed as:

$$u(x,\omega) = U_0(\omega)e^{-jk_0(\omega)\cdot x} \quad (10)$$

where $U_0$ defines the amplitude and the polarization of the wave at the considered frequency, and $k_0(\omega) = k_0(\omega)i_1' = k_0(\omega)(\cos\theta i_1 + \sin\theta i_2)$ is the considered wave vector defining plane wave propagation at an angle $\theta$ (FIG. 2). Assuming that the considered wave is characterized by a displacement field such that:

$$u(x,\omega) \cdot i_2' = 0 \quad (11)$$

The only strain component relevant to the surface mounted sensor is given by:

$$\varepsilon_{1'1'} = \frac{\partial u_1'}{\partial x_1'} = jU_{1_0'}(\omega)k_0(\omega)e^{-jk_0(\omega)x_1'} \quad (12)$$

while $\epsilon_{2'2'} = \gamma_{1'2'}$. In this case, the plane strain field in equation (9) can be written as:

$$\epsilon = \epsilon_{1'1'}[\cos^2\theta, \sin^2\theta, 0]^T \quad (13)$$

$$\epsilon = \epsilon_{1'1'} r(\theta) \quad (14)$$

Substituting equation (13) into equation (9) gives:

$$V(\omega) = jU_{1_0'}(\omega)k_0(\omega)H(\theta)D(\omega,\theta) \quad (15)$$

where:

$$H(\theta) = \frac{t_P}{A_P} \frac{b^T d^\sigma C^E r(\theta)}{[b^T(d^\sigma C^E d^{\sigma^T} - e^\sigma)b]} \quad (16)$$

and $$D(\omega,\theta) = \int_\Omega e^{jk_0(\omega)(x_1\cos\theta + x_2\sin\theta)} f(x)dx \quad (17)$$

define two separate contributions to the measured voltage. The first quantity H contains the material properties of the piezo-structure system, and can have a directional component in case of non-isotropic properties. For the case of a PZT 5H material, whose properties are listed in TABLE 1, the quantity H is constant with respect to the angle of wave propagation $\theta$, and therefore no directionality is introduced. Other common piezo patches, such as the Macro Fiber Composite sensors, have non-isotropic piezoelectric properties which lead to significant directional behaviors.

In contrast, parameter D describes the effect of the distribution of material as defined by the function $f(x)$. Specifically, the definition of D provides the opportunity of selecting specific material and polarization distributions to tune the sensor to specific wavelengths and associated wave modes, and to achieve desired directionality properties. Of interest, is the further development of equation (17), which can be rewritten as follows:

$$D(\omega,\theta) = \int_{-\infty}^{+\infty} e^{-jk_0(\omega)\cdot x} f(x)dx \quad (18)$$

which exploits the limited support of the function $f(x)$ so that the integration limits can be extended to infinity without affecting the value of the integral. Equation (18) can be easily recognized as the spatial Fourier Transform (FT) of the function $f(x)$, with the understanding that its dependence upon frequency is based on its direct relation with the wave vector $k_0(\omega) = k_0(\omega)(\cos\theta i_1 + \sin\theta i_2)$ as defined by the dispersion relations for the considered medium. This simple observation leads to the convenient estimation of the directivity for various sensor shapes and polarizations through the identification of the proper FT pairs:

$$D(k_0(\omega),\theta)=F[f(x)] \quad (19)$$

where $F[\bullet]$ denotes the FT. Equation (19) suggests the possibility of evaluating the sensor directivity through FFT algorithms in the case of complex material distributions.

At the same time, given a desired directivity, it is possible to obtain the correspondent sensor geometry simply inverting Equation (19):

$$f(x)=F^{-1}[D(k_0(\omega),\theta)] \quad (20)$$

where $F^{-1}[\bullet]$ denotes the inverse FT.

TABLE 1

| PZT 5H Piezoelectric Material Characteristics | | |
|---|---|---|
| $c_{11}^E = 1.27 \times 10^{11}$ Pa | $c_{22}^E = 1.27 \times 10^{11}$ Pa | $c_{33}^E = 1.17 \times 10^{11}$ Pa |
| $c_{12}^E = 8.02 \times 10^{10}$ Pa | $c_{13}^E = 8.46 \times 10^{10}$ Pa | $c_{23}^E = 8.46 \times 10^{10}$ Pa |
| $c_{44}^E = 2.30 \times 10^{10}$ Pa | $c_{55}^E = 2.30 \times 10^{10}$ Pa | $c_{66}^E = 2.34 \times 10^{10}$ Pa |
| $\epsilon_0 = 8854 \times 10^{-12}$ F/m | $d_{15} = 741 \times 10^{-12}$ C/N | $d_{24} = 741 \times 10^{-12}$ C/N |
| $d_{31} = -274 \times 10^{-12}$ C/N | $d_{32} = -274 \times 10^{-12}$ C/N | $d_{33} = 593 \times 10^{-12}$ C/N |
| $\epsilon_{11}^\sigma = 3130\epsilon_0$ | $\epsilon_{22}^\sigma = 3130\epsilon_0$ | $\epsilon_{33}^\sigma = 3400\epsilon_0$ |

Frequency Steerable Acoustic Transducer Spiral Array

The frequency-dependent directivity of the sensor presented in equation (19) suggests the possibility of designing the material distribution in order to obtain desired directionality at specified frequency. One strategy is to design a sensor whose directionality can be achieved through a sweep of frequencies, so that there is a unique relation between frequency of maximum sensitivity and direction of wave propagation. Based on the discussion previously presented such a performance may be achieved by specifying the directivity of the sensor as a function of the wave vector $k_0(\omega)$, to then obtain the corresponding spatial distribution of the material through an inverse FT in space, as showed in equation (19). A desired directivity distribution features a single lobe at angles which vary with the frequency and the associated wave vector of the incoming wave. Such configuration corresponds to a directivity function with maxima defining a spiral in the wavenumber domain. The desired directivity function can be expressed as follows:

$$D(k_0(\omega), \theta) = -j\frac{1}{N}\sum_{n=1}^{N}[\text{sinc}(a|k_0 - k_n|) - \text{sinc}(a|k_0 + k_n|)] \quad (21)$$

Figure 3:
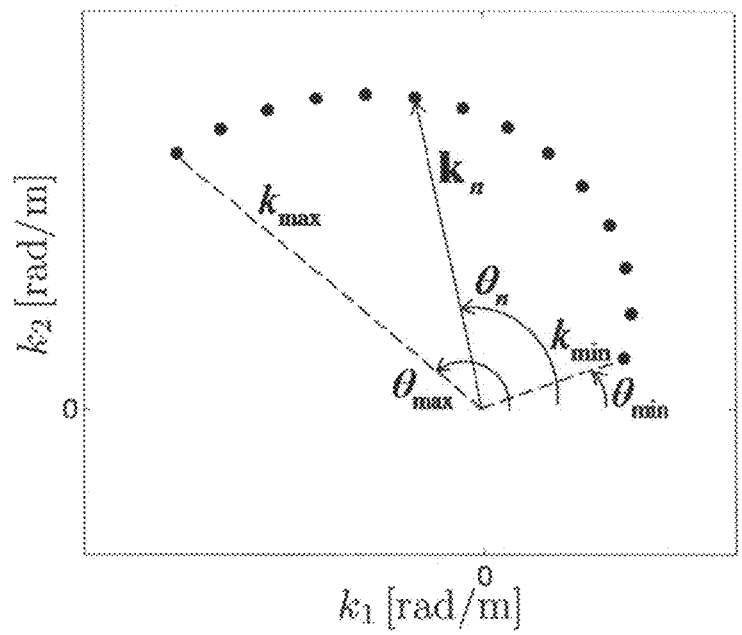
FIG. 3: Geometrical parameters of the spiral.

In equation (21), the wave vector $k_n$ corresponds to the angle at which the n-th maximum of the spiral is located, and therefore where the corresponding lobe occurs, according to the following expression:

$$k_n = \left[(k_{max} - k_{min})\frac{\theta_n - \theta_{min}}{\theta_{max} - \theta_{min}} + k_{min}\right)(\cos\theta_n i_1 + \sin\theta_n i_2)\right] \quad (22)$$

which defines the shape of an Archimedean spiral[i]. The N angular positions of the points, $\theta_n$, are determined such that the N-1 arcs, in which the spiral is divided, are of constant length (FIG. 3).

Figure 4:
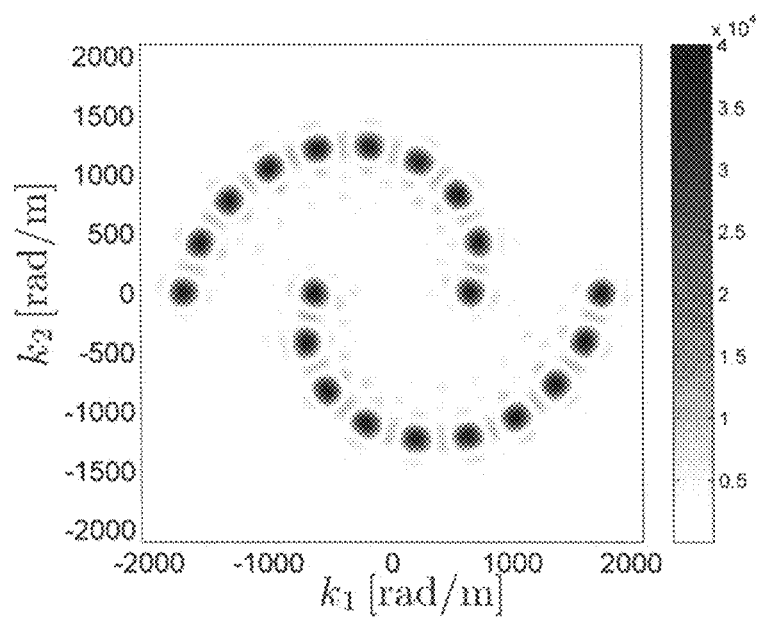
FIG. 4: Spiral directivity function.
Figure 5:
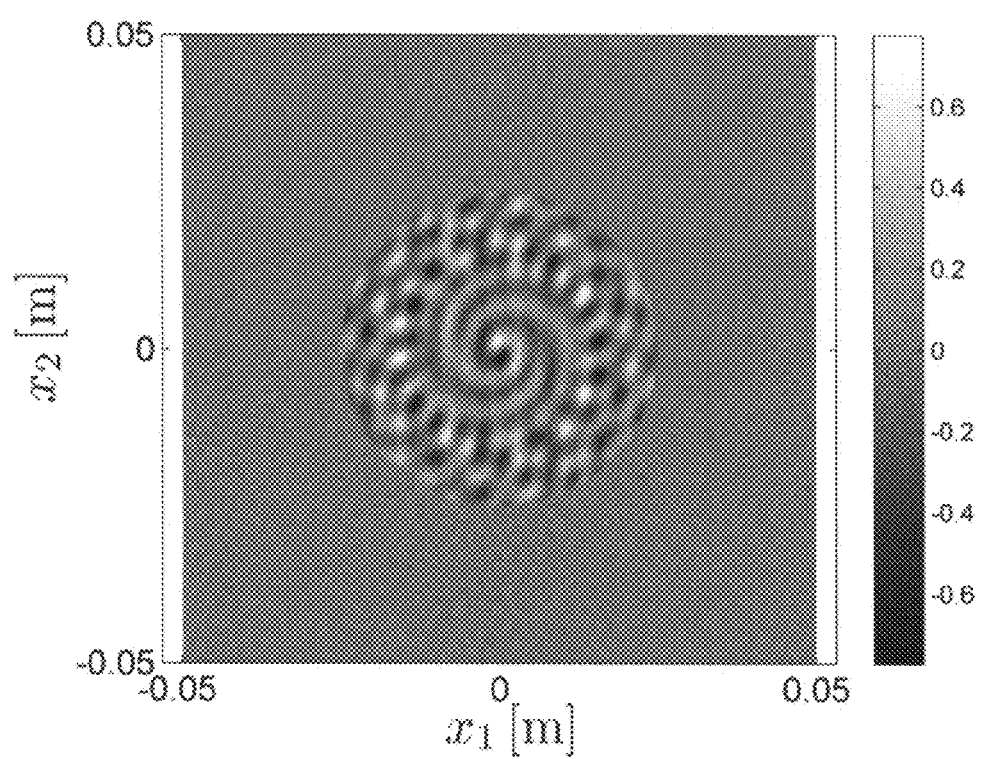
FIG. 5: Spatial distribution corresponding to the function $f(x)$ in equation (23).

The spiral of equation (22) is also defined in terms of minimum and maximum values for the wave vector amplitudes, respectively denoted as $k_{min}$ and $k_{max}$, which correspond to maximum sensitivities occurring respectively at $\theta=\theta_{min}$ and $\theta=\theta_{max}$. These bounds on the wave vector's amplitude can be translated in frequency limits for the sensor directional sensitivity, and therefore essentially define the bandwidth of the sensor. FIG. 4 shows the directivity of a spiral with sensing directions N=10, with $\theta_{min}=0$, $\theta_{max}=\pi$, $k_{min}=650$ rad/m and $k_{max}=1750$ rad/m. The corresponding spatial distribution for a radius of the patch equal to a=25 mm is shown in FIG. 5, where the gray background corresponds to a value of 0, while the dark regions are associated with negative values, while the light regions defined positive polarization.

Figure 6:
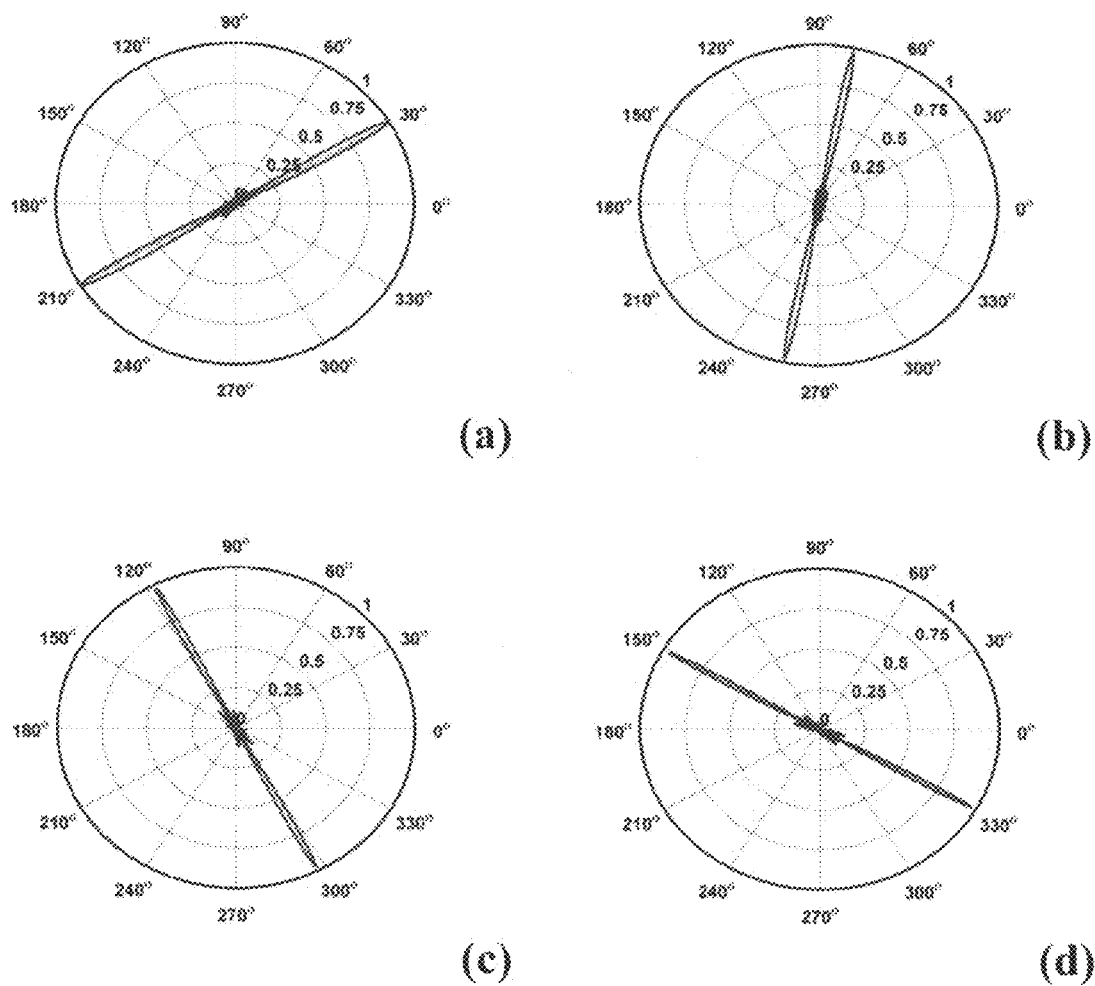
FIG. 6: Spatial directivity curves for various $\theta_n$.

Examples of the directivities obtained at a selected number of angles are presented in FIG. 6.

The spatial distribution corresponding to equation (23) is obtained using equation (20). It is worth noting how the sum of two sinc functions in equation (21) has been introduced in order to ensure that the corresponding inverse transform leads to a real valued function $f(x)$, whose expression is:

$$f(x) = \frac{1}{N}\text{rect}\left(\frac{|x|}{a}\right)\sum_{n=1}^{N}\sin(k_n \cdot x) \quad (23)$$

The spatial distribution described by equation (23) corresponds to a configuration that is practically unfeasible. A simple strategy involves the application of a thresholding procedure which transform $f(x)$ in a step function distributed over the considered domain. A tolerance value $\epsilon$ is introduced as a percentage of the maximum of $f(x)$, so that the final spatial distribution function can be described as follows:

$$\bar{f}(x) = \begin{cases} 1, & f(x) \leq \varepsilon \\ 0, & f(x) < |\varepsilon| \\ -1, & f(x) \leq -\varepsilon \end{cases} \quad (24)$$

Figure 7:
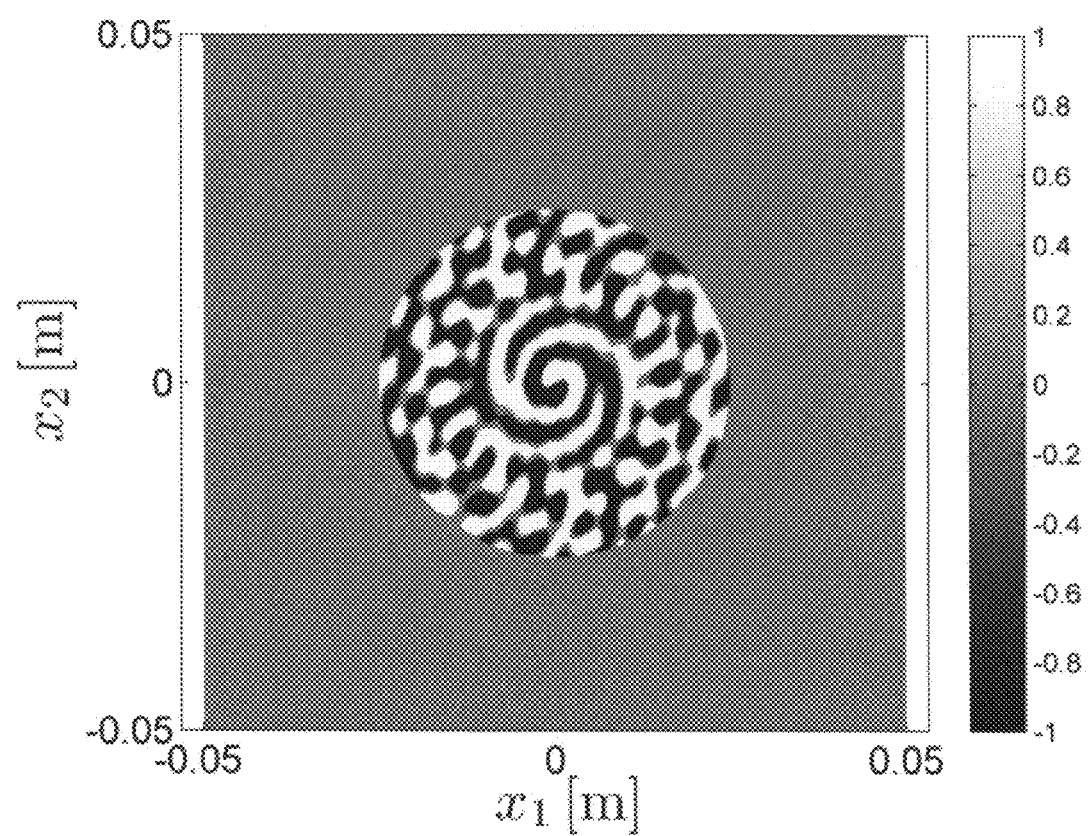
FIG. 7: Spatial distribution corresponding to the thresholded spiral $\tilde{f}(x)$ expressed in equation (24).
Figure 8:
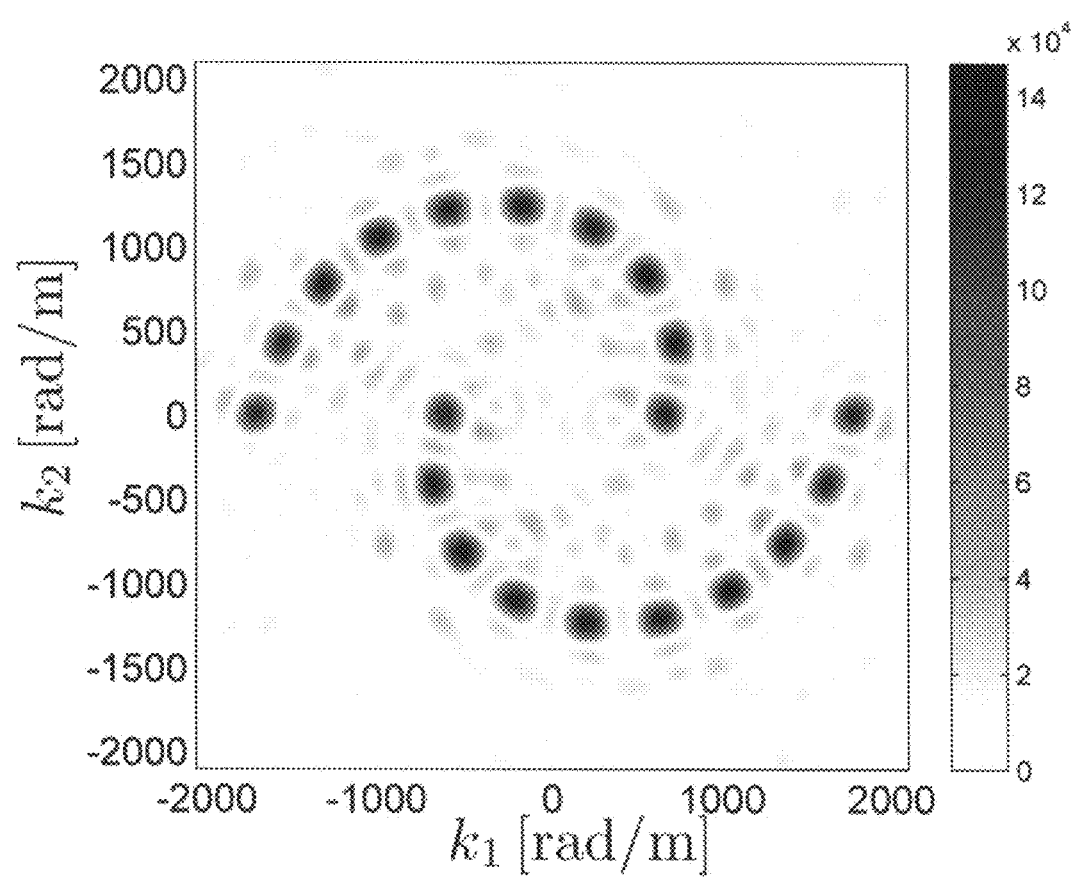
FIG. 8: Spiral directivity function corresponding to the thresholded spiral $\tilde{f}(x)$ expressed in equation (24).

The obtained distribution corresponding to a tolerance level of $\epsilon=7\%$ of the maximum of $f(x)$, is presented in FIG. 7, which shows areas in black and white corresponding respectively to negatively and positively polarized electrodes. The corresponding directivity is obtained through the numerical evaluation of the associated FT and it is shown in FIG. 8.

The peculiarity of this sensor is to act as a spatial filter. For an incoming wave along $\theta_n$ direction, it acts as a narrow band pass filter centered at $|k_n|$. Through the dispersion relation of the elastic media, from wavenumber $|k_n|$ it is possible to obtain the value of the frequency which is associated with $\theta_n$, and so expect a spectra of the sensor output signal with a marked peak for this frequency.

Numerical Evaluation

The performance of the spiral array defined in FIG. 5 is here evaluated numerically. For the numerical simulation the transducer is used in actuation mode. In this case it is supposed to be driven at a certain frequency to generate guided waves in a specific direction. Due to the complicated shape of the transducer, this is discretized in a set of very small circular discs. Then the plate response is computed as a superposition of the contributions of the individual circular discs, weighted with the value that $f(x)$ assumes in the center of each disc location, following a semi-analytical procedure.

Dispersion Relation

Figure 9:
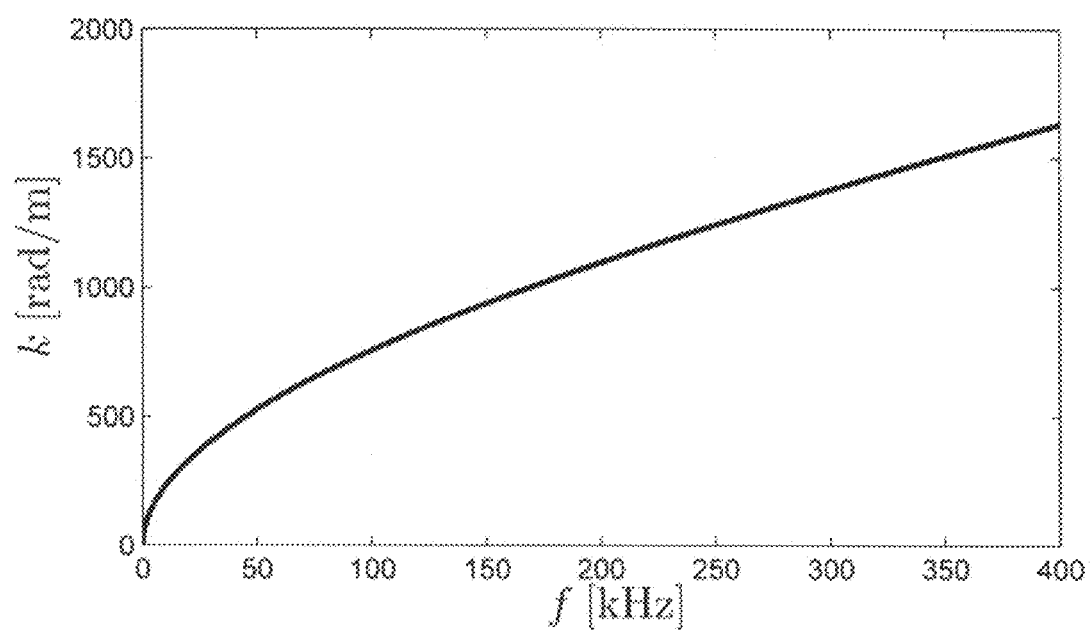
FIG. 9: Dispersion relation for an Aluminum plate of 0.75 mm thickness ($A_0$ mode).

The spiral array is completely defined in space and wavenumber domain. To link the properties in wavenumber domain to the frequency domain, it is necessary to know the dispersion relation of the elastic medium on which the sensor is mounted. In FIG. 9 the dispersion relation in the case of an aluminum plate with thickness equal to 0.75 mm is shown, which is the case considered in our experiment. More specifically it is the dispersion relative to Lamb waves, $A_0$ mode.

Numerical Results

The directions chosen for the guided wave generation are the same as those shown in FIG. 6. Thus, using the same $\theta_n$, with the corresponding $k_n$ (see equation (22)) it is possible to establish the relative excitation frequency, $f_n$, through the dispersion relation of FIG. 9.

Figure 10:
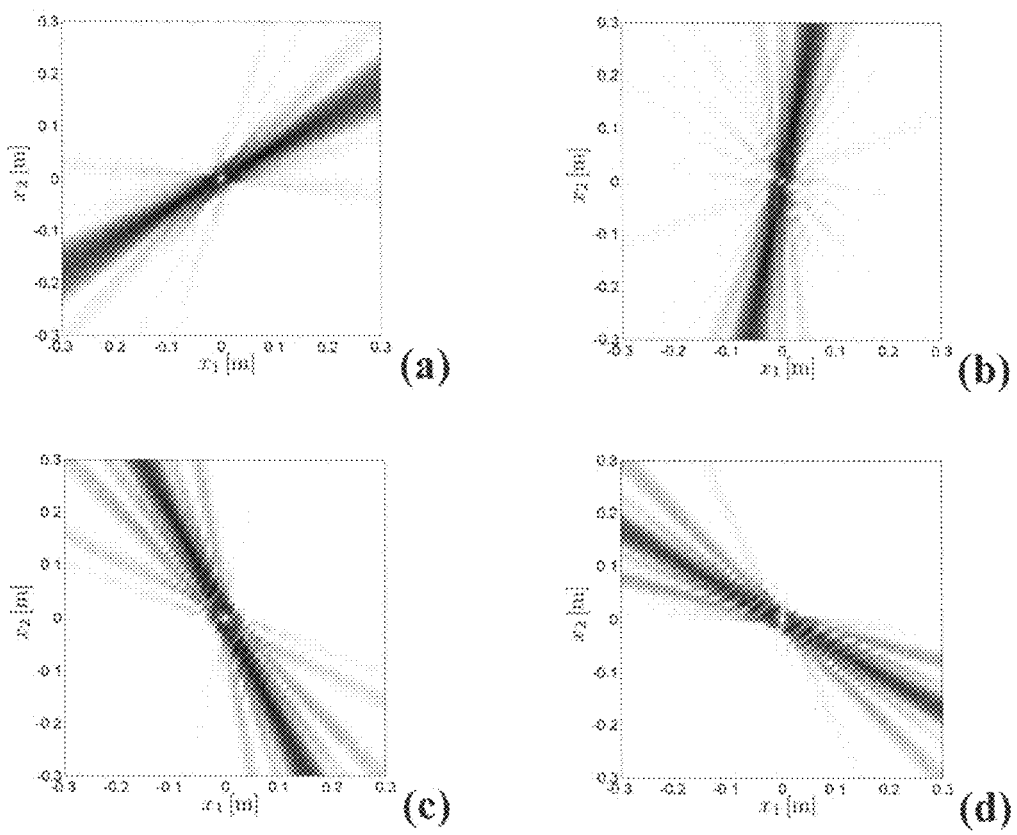
FIG. 10: Plate response for selected excitation frequencies $f_n$.

FIG. 10 presents the plate out-of-plane response to harmonic excitations at these frequencies $f_n$. The plots clearly show the directional characteristics of radiation, and confirm the radiation directions predicted by the directivities of FIG. 6.

Experimental Evaluation

A prototype of the spiral array is not yet available; for this reason a virtual approach using a laser vibrometer has been developed to perform a preliminary experimental validation of its capabilities.

Experimental Setup

The idea is to test the spiral array in a case of impact detection. Considering to have a plate which receives an impact, if the spiral array was mounted on the plate, it would be possible trying to determine the direction of the impact with respect to the sensor itself. This situation is reproduced in lab with two variations: the impact is replaced by a PZT transducer excited with a broad band pulse; no sensor is applied on the plate and the area, where should have been placed it, is scanned with a Scanning Laser Doppler Vibrometer (SLDV). The data set of the recorded points is then weighted with a mask which simulates the action of the sensor and in the following this passage will be made clear.

Figure 11:
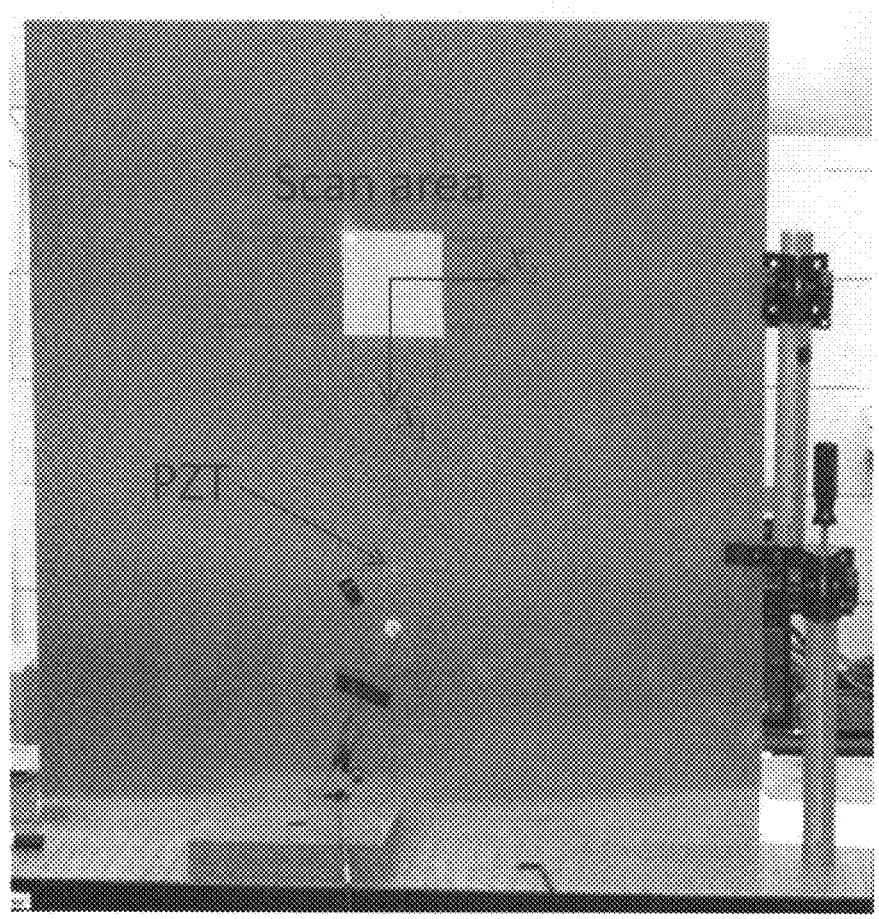
FIG. 11: Experimental setup.

Specifically, a 6061 aluminum plate of dimension 1 m×1 m×0.75 mm was used. On top of it, a 5 mm diameter PZT transducer was mounted. A 100 mm×100 mm scan area was set at a distance of 280 mm from the PZT disc location. In FIG. 11 the experimental setup is depicted.

The PZT was driven by broadband pulses from a Panametrics-NDT 5058PR pulser. For better signal-to-noise ratio, the excitation output voltage is around 900 V. At the 900 V level, the pulser has the 10%-90% rise time $t_{rise} \leq 40$ ns. The bandwidth of the pulse can be estimated as BW=$0.35/t_{rise}$=8.75 MHz, which is wide enough to excite the bandwidth of interest (<300 kHz).

The wavefield of the scan area is recorded by a Polytec PSV400M2 SLDV placed at a distance of 3 m from the plate. The SLDV was set to filter out unwanted frequency components by using a bandpass filter ranging from 10 to 500 kHz.

Data Acquisition

The scan area is spanned by a grid of M×m points, with M equal to 128. The generic position of a scan point is defined as $x_j$, and the time history of the out-of-plane displacement recorded for the same point is $g_j(t)$. The visualization of the scan grid is presented in FIG. 12.

Figure 13:
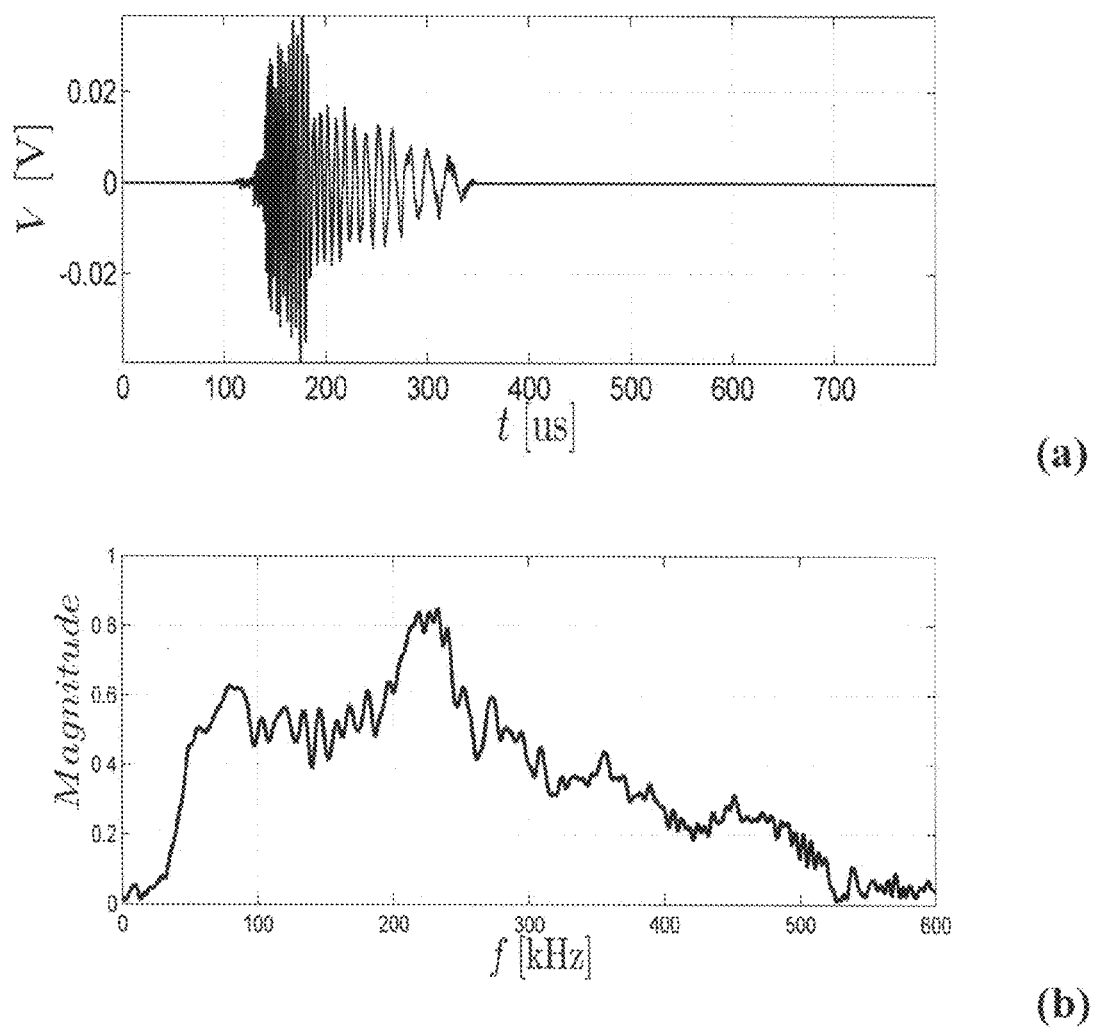
FIG. 13: Time history and spectrum of a generica acquisition $g_j$ corresponding to $x_j$ location.

A generic acquisition $g_j(t)$ and its spectrum are shown in FIG. 13. It can be seen as the frequency content of the signal to be processed, i.e. filtered, by the spiral array. The filtering action is hereby accomplished through the mask procedure. The $g_j$ spectrum should be flat and broad band as much as possible to not bias the filtering and get the best results. For this aspect, the spectrum in the figure is not optimal, but it can be used anyway as a first evaluation.

Sensor Design

Two sensors, named sensor a and sensor b, have been chosen to filter the signals acquired with the laser. The wavenumber spiral is the same for both, and its parameters are listed in TABLE 2.

TABLE 2

Wavenumber Spiral Parameters.

| | |
|---|---|
| N | 22 |
| $k_{max}$ [rad/m] | 1500 |
| $k_{min}$ [rad/m] | 550 |
| $\theta_{max}$ [deg] | 120 |
| $\theta_{min}$ [deg] | 0 |

The sensors are differentiated by the size, represented by a, and the threshold procedure is applied only to sensor b with $\epsilon$=15%. In TABLE 3 the size of the sensors is indicated.

TABLE 3

Sensors Size

| sensor | a [mm] |
|---|---|
| a | 50 |
| b | 25 |

Figure 14:
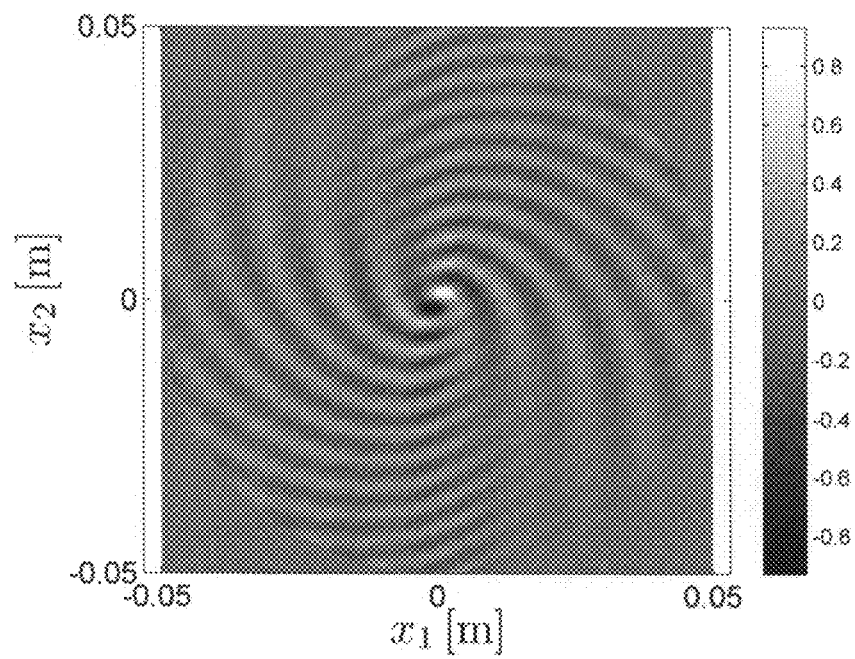
FIG. 14: Adopted sensors: (a) sensor a, (b) sensor b.
Figure 14:
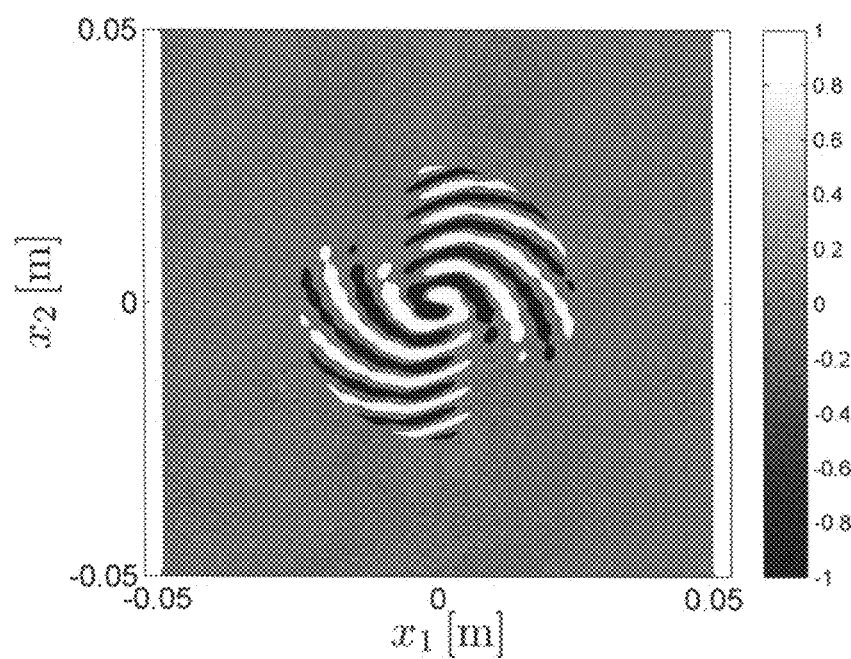
Figure 15:
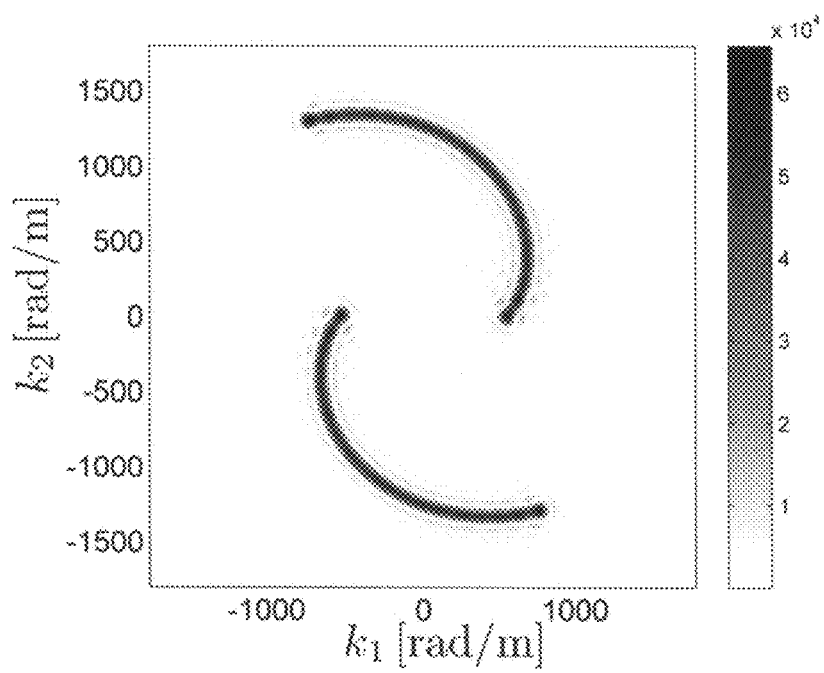
FIG. 15: Directivity of adopted sensors: (a) sensor a, (b) sensor b.
Figure 15:
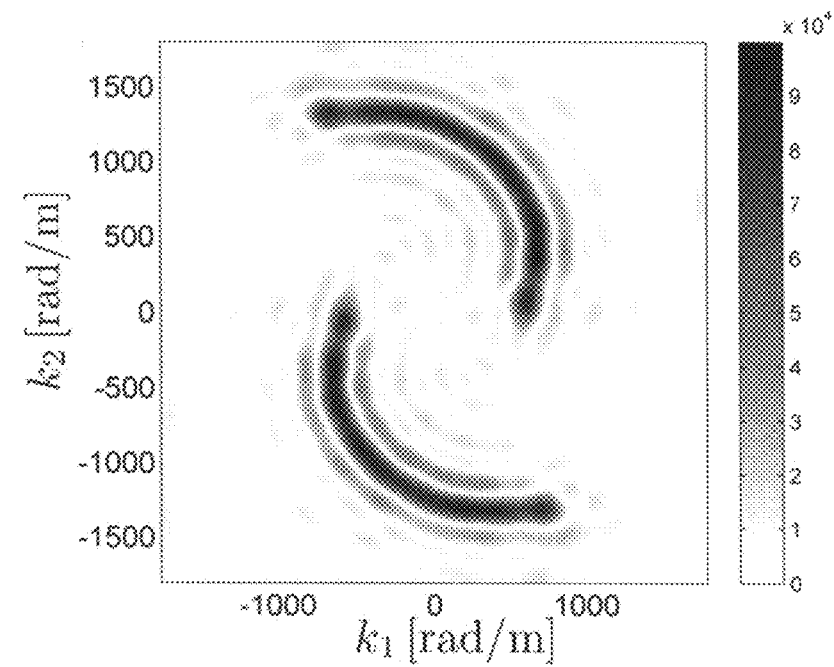

In FIG. 14 the sensors are depicted simply plotting $f(x)$ for sensor a and $\tilde{f}(x)$ for sensor b evaluated with parameters values of TABLE 2 and TABLE 3. To evaluate their filtering performances, it is better look at them in the wavenumber domain; this means taking the 2D-FT of $f(x)$ and $\tilde{f}(x)$, and thus plotting the directivity (FIG. 15). In this domain, it is clear why they are called spiral arrays: the maxima of the spectra are located along the spiral defined in equation (22).

Going from sensor a to sensor b, there is an impoverishment of performances. In case a, the maxima are confined along a narrow spiral. This means a narrow band filtering in frequency, crucial to obtain a good estimation of $\theta$, defined in FIG. 2, which can also be seen as the direction of arrival (DOA). In case b, the spiral is wider, and there is the presence also of more evident side lobes. This leads to a poorer resolution in DOA detection. At the same time, solution b is more compact, because it is just half of the size of a.

The spirals of directivities shown in FIG. 15 appear to be continuous, differently to those presented in FIG. 4 and FIG. 8 that are discrete. This is due to a bigger value of N and consequently the maxima of adjacent angular positions are so close to be not separated. The achievement of this continuity is a positive effect for the sensor, because in this way it can sense continuously all directions inside its range from $\theta_{min}$ to $\theta_{max}$.

With the dispersion relation given in FIG. 9 and the spiral defined in equation (22) with values listed in TABLE 2, it is possible to build a correlation map between the angular positions, $\theta_n$, and the frequency associated with correspondent wavenumber $k_n$. Thus, for each $k_n(\theta_n)$, defined from equation (22) as:

$$k_n(\theta_n) = \frac{k_{max} - k_{min}}{\theta_{max} - \theta_{min}} \theta_n + \left( k_{min} - \frac{k_{max} - k_{min}}{\theta_{max} - \theta_{min}} \theta_{min} \right) \quad (25)$$

a frequency $f_n(\theta_n)$ is determined through the dispersion relation. Because, as noticed earlier, the directivity of the considered sensors appears to be continuous, it is reasonable to delete the subscript n from equation (25) and build a continuous θ-frequency map as showed in FIG. 16.

Mask Procedure

Figure 12:
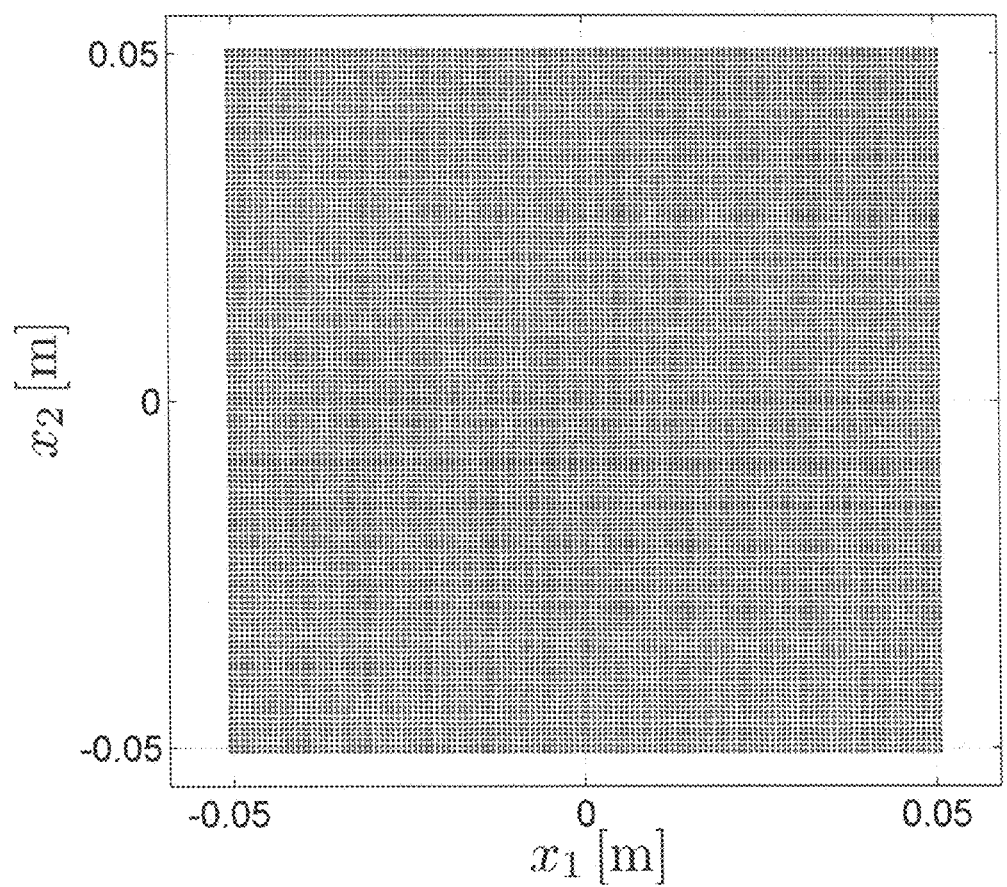
FIG. 12: 128×128 points scan grid: for each $x_j$ is collected $g_j(t)$, with j=1 ... $128^2$.
Figure 17:
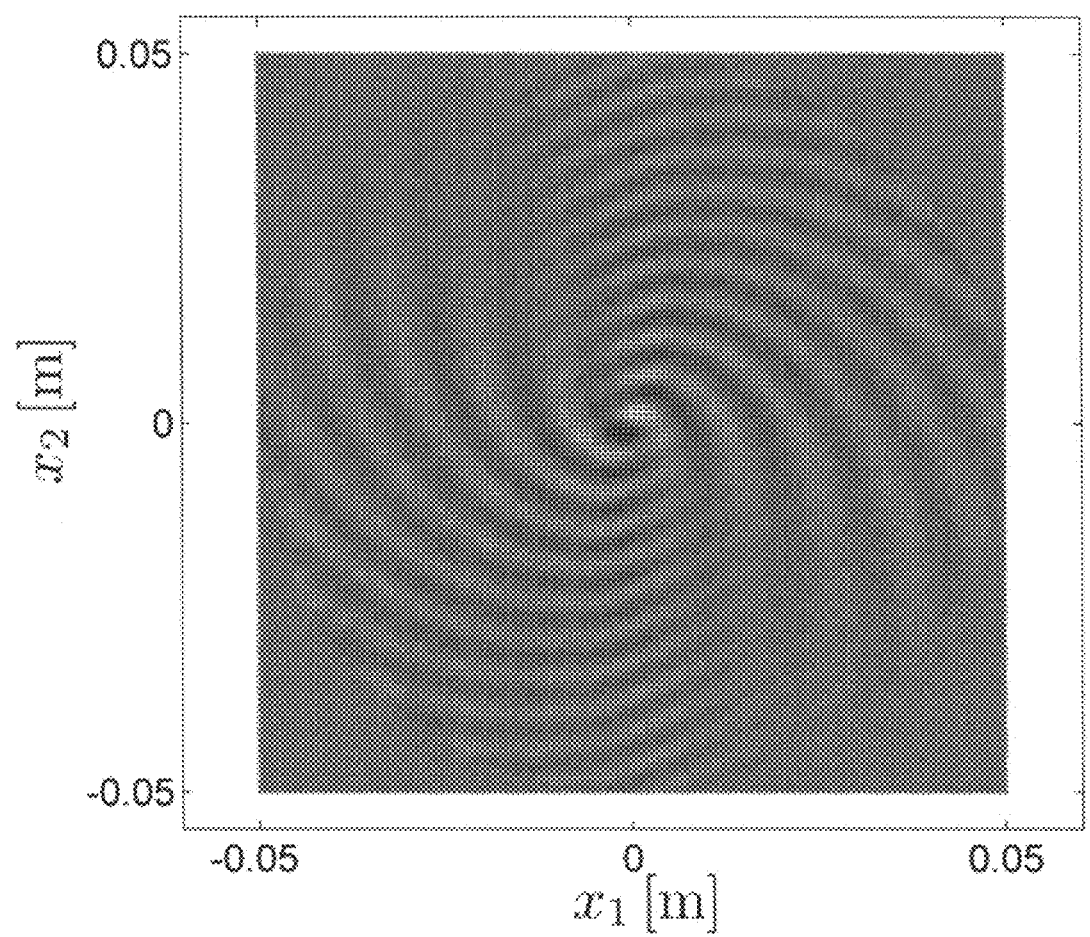
FIG. 17: Spiral array mask sensor a::$f(x)$ is sampled at each $x_j$ (red dots), obtaining $f(x_j)$, with j=1 ... $128^2$.

The mask procedure mentioned above comprises extracting a mask from the sensors chosen for the analysis (FIG. 14). The sensor is supposed to overlap the scan area and the mask is anything else than a sampling of $f(x)$, or $\bar{f}(x)$ for the thresholded case, in correspondence of all the points $x_j$ scanned with the laser (FIG. 12). In FIG. 17 this sampling is shown for the case of sensor a. In this way, for each $g_j$, it is associated the local contribution of the sensor $f(x_j)$.

The action of the sensor is then replaced weighting $g_j$ with $f(x_j)$ and then summing all the weighted time histories to obtain Q(t) which is considered the output that the spiral sensor would give:

$$Q(t) = \sum_{j=1}^{M^2} f(x_j) g_j(t) \quad (26)$$

Figure 18:
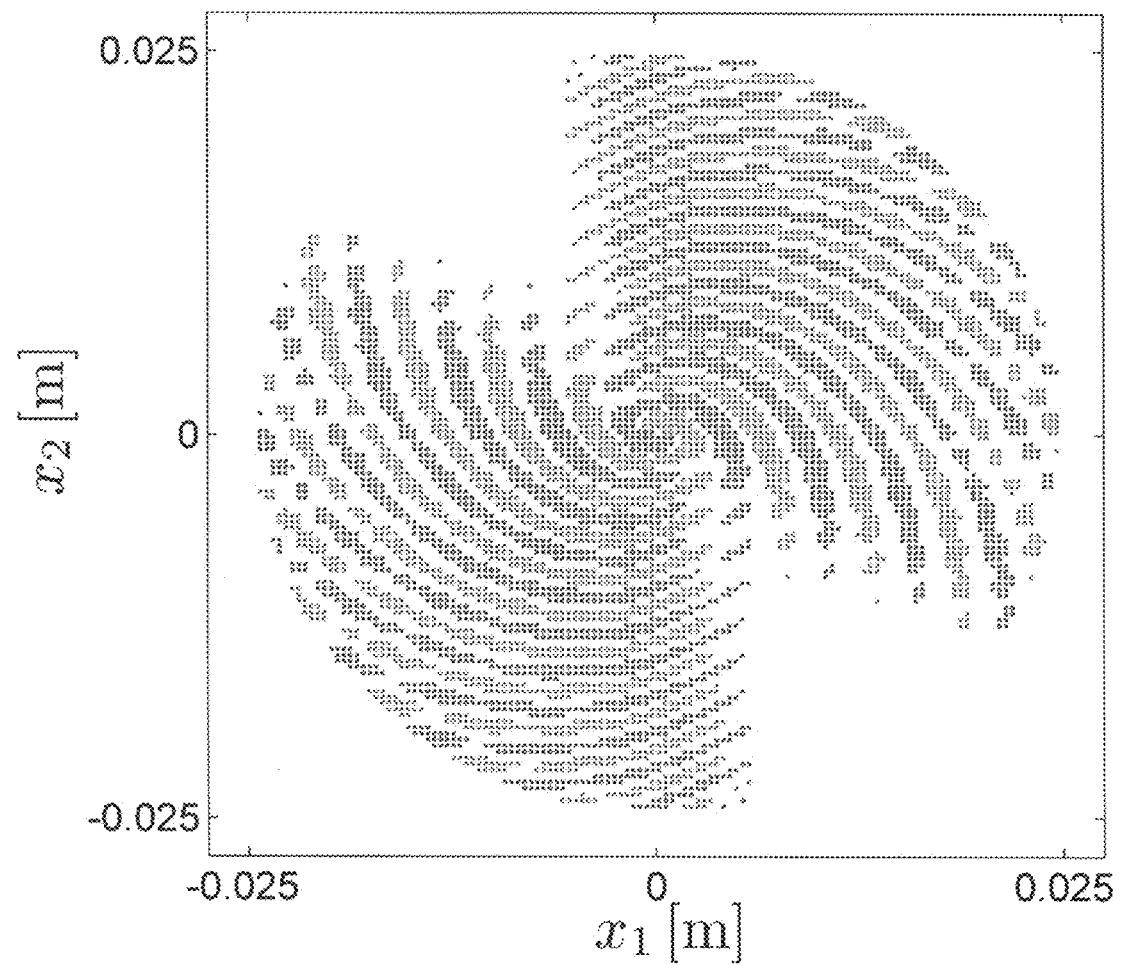
FIG. 18: $\tilde{f}(x_j)$ for sensor b: red dots are the locations in which $\tilde{f}(x_j)=1$, blue dots are the locations in which $\tilde{f}(x_j)=-1$.

In the case of sensor b, $\bar{f}(x_j)$ replaces $f(x_j)$. In FIG. 18 the element of the mask $\bar{f}(x_j)$ different from zero are showed. It is an effective graphical way to see how the scan points of FIG. 12 are weighted in the thresholded case: basically only those scan points associated with an $\bar{f}(x_j)\neq 0$ are used in computing the sensor output.

Virtual Spiral Array Application

From the experimental setup of FIG. 11, it is clear that the DOA for the scan area is 0 deg. To test the sensors in different directions, it has been supposed to mount them at different orientations with respect to the DOA of the pulse. These orientations are angles θ's collected in TABLE 4. Computationally this means to build masks according to the following variation of equation (23):

$$f(x_j) = \frac{1}{N} rect\left(\frac{|x|}{a}\right) \sum_{n=1}^{N} \sin(k_n \cdot x - \theta) \quad (27)$$

TABLE 4

Sensors Orientation Angles And Relative Frequencies

| θ [deg] | 10 | 30 | 50 | 70 | 90 | 110 |
|---|---|---|---|---|---|---|
| f [kHz] | 70 | 108 | 152 | 202 | 257 | 315 |

Figure 16:
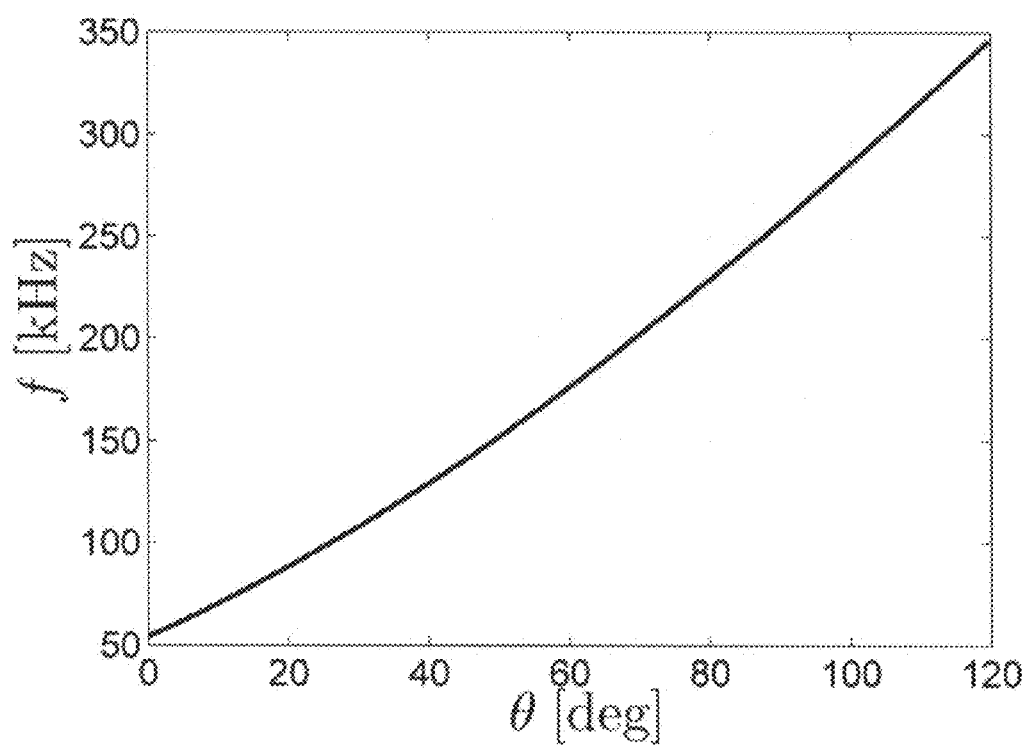
FIG. 16: Spiral array θ-frequency correlation map.

In TABLE 4, for each θ, also the associated frequencies are listed, obtained via the θ-frequency map of FIG. 16.

Figure 19:
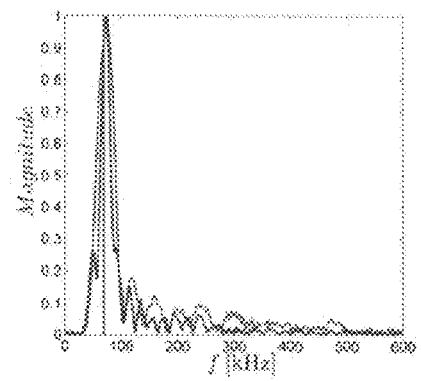
FIG. 19: Comparison between the two spiral arrays for different angles θ: black line, sensor a; blue line, sensor b; red vertical line, expected peak frequency.
Figure 19:
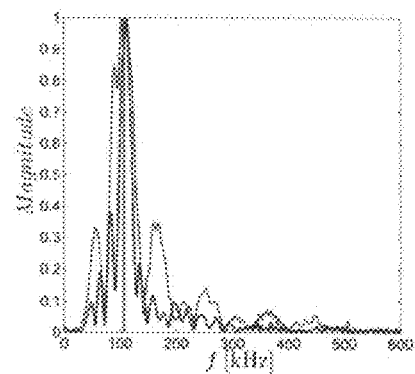
Figure 19:
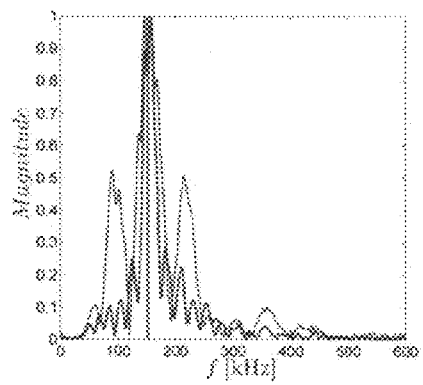
Figure 19:
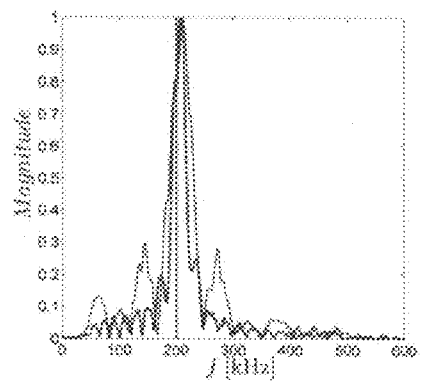
Figure 19:
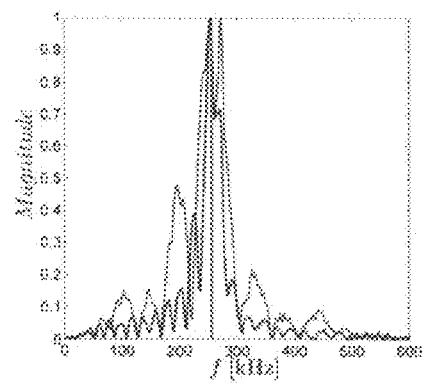
Figure 19:
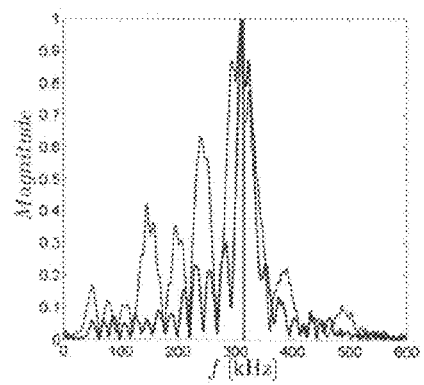

In FIG. 19, the spectra of the virtual outputs of sensors, Q, defined in equation (26), are plotted for the various θ.

In TABLE 5 the peak frequencies obtained with the two sensors for the various orientations θ's are collected. From these last, using the θ-frequency correlation map of FIG. 16, the DOA's can be estimated and are presented in TABLE 6.

TABLE 5

Expected Peak Frequencies Vs Observed Peak Frequencies For Sensors a And b

| | | f [kHz] | | | | | |
|---|---|---|---|---|---|---|---|
| Expected | | 70 | 108 | 152 | 202 | 257 | 315 |
| sensor | a | 74 | 112 | 158 | 209 | 254 | 311 |
| | b | 75 | 112 | 146 | 212 | 272 | 310 |

TABLE 6

Expected DOA's Vs Detected DOA's By Sensors a And b Obtained Through The θ-Frequency Correlation Map.

| | | θ[deg] | | | | | |
|---|---|---|---|---|---|---|---|
| Expected | | 10 | 30 | 50 | 70 | 90 | 110 |
| sensor | a | 12 | 32 | 52.5 | 72.6 | 89 | 108.5 |
| | b | 12.8 | 32 | 47.4 | 73.8 | 95.4 | 108.1 |

From the results presented in FIG. 19, TABLE 5 and TABLE 6, it is possible to observe a very good performance of the sensors. As expected sensor a behaves better than the other, but sensor b still shows good capabilities. The sensors filter the input signal quite sharply around the expected frequency.

The design of a transducer which allows a frequency based direction of arrival detection has been presented and its capabilities have been explored numerically and experimentally through a virtual approach based on laser vibrometry. Minimum hardware and software are required as the detection of the direction of arrival is achieved measuring the sensing frequency. This approach is characterized by very attractive properties, as limited hardware requirements, robustness and single channel control. Very promising results have been obtained. Future work is necessary for the practical realization of the sensor.

WS-FSAT Prototype Fabrication

The substrate material used for WS-FSAT prototyping is a 110-µm-thick PVDF film metallized on both sides with 40 µm of Copper covered by 15 µm of Nickel. The piezo film sheets are supplied by Measurement Specialties, Inc., Hampton, Va. The process flow is described below and aims at patterning the metallization on both sides of the PVDF film according to the desired electrodes' shape using typical microfabrication techniques.

Preparation:

The PVDF substrate is attached to a carrier wafer and sealed to it by adhesive tape so that all the subsequent steps only affect the exposed surface.

Resist Coating:

The sample is spin coated with positive photoresist (Microposit SC 1827). The coated sample is baked for 30 minutes at 90° C. to allow for solvent evaporation.

TABLE 7

Specifications of the fabricated WS-FSAT prototype (the bandwidth indication refers to A0-mode sensitivity in a 0.75-mm-thick Al plate).

| Outer Diameter | Directional Range | Wavenumber Range | Active Bandwidth |
|---|---|---|---|
| 65 mm | 65 mm [0°, 180°] | [508, 1509] rad/m | [50, 350] kHz |

Photolithography:

The electrodes' geometry is printed on the resist layer by exposing the sample to 405 nm ultraviolet (UV) light through a chrome/soda lime mask (supplied by Photo Sciences, Inc., Torrance, Calif.) reporting the desired shape. Exposed areas of the photoresist become soluble through specific substances (see next step).

Development:

A 3.5:1 solution of distilled water and Microposit 351 developer is used to remove the exposed resist, so that only the printed features are left.

Wet Etching:

A 15% solution of Ferric Chloride (FeCl3) allows removing the metal on surface portions that are not protected by photoresist.

Stripping:

The protective resist is stripped away using acetone and the sample is cleaned with methanol and isopropanol.

After processing the top surface, the sample is removed from the carrier wafer, flipped and attached to a transparent carrier wafer to process the back side. All the process steps above are repeated, but photolithography now requires careful alignment between top and bottom electrodes. This operation is facilitated by alignment marks printed on the masks. The outlined process flow was applied to fabricate the prototype device with specifications reported in TABLE 7, exploiting cleanroom facilities of the Nanotechnology Research Center (NRC) at Georgia Tech.

Figure 20:
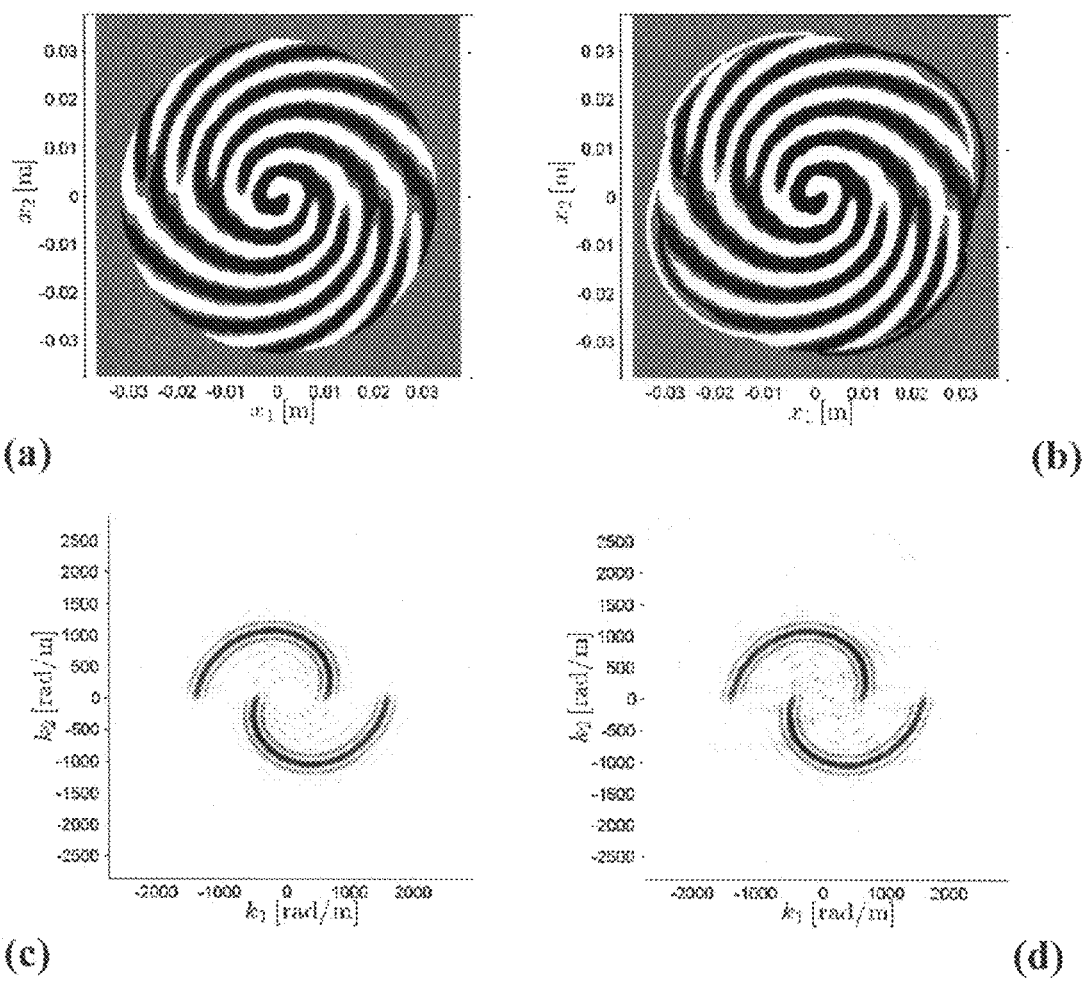
FIG. 20: (a) Electrodes' geometry for the FSAT described in TABLE 7 and (c) corresponding wavenumber distribution. (b) Modified design which includes electrical connections between individual portions of each electrode. (d) Slight perturbation of the wavenumber performance due to the additional electrical connection paths.

The transducer geometry derived from wavenumber design and thresholding is reported in FIG. 20(a), where black and white areas represent two separate electrodes. The original design was modified to that of FIG. 20(b) to include electrical connections between individual portions of each electrode. Such changes in the design do not significantly affect the wavenumber distribution of the electrodes, which still resembles closely the original, quantized design. This is shown by a comparison of wavenumber distributions presented in FIG. 20(c) and FIG. 20(d), which respectively correspond to the original design and to the modified configuration with electrical connections.

Figure 21:
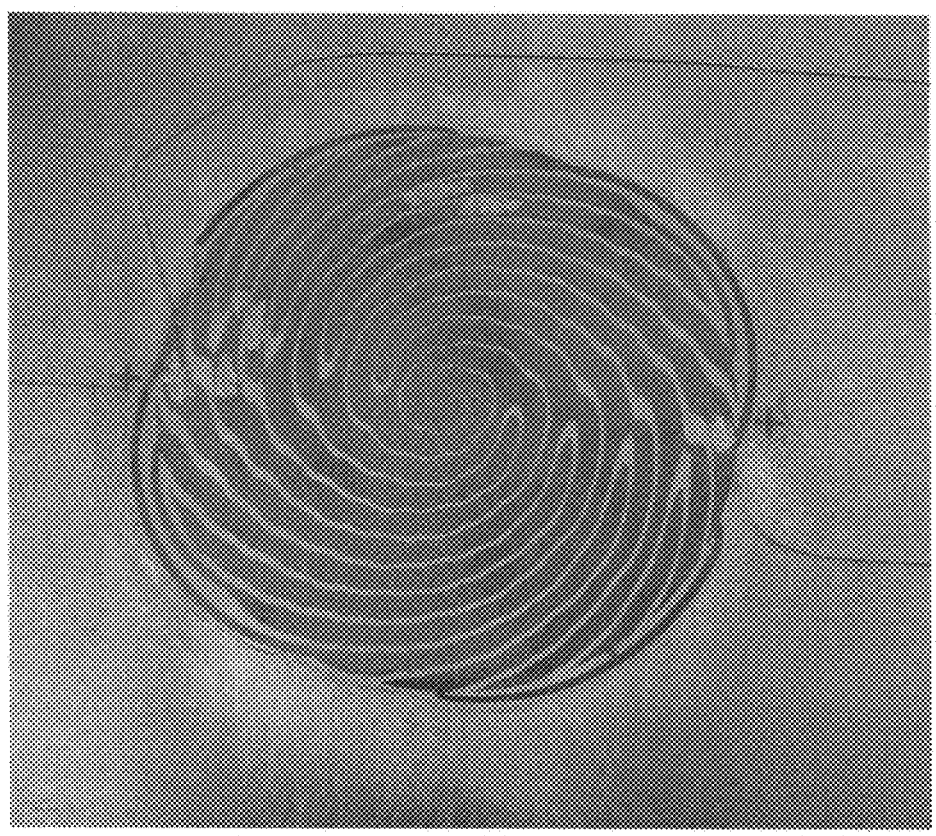
FIG. 21: Prototype FSAT with specifications in TABLE 7. A few patches of conductive glue meant to repair microfractures in the metallization are visible. The sensor is attached to a 0.75-mm-thick Al plate. The electrical wires used to transmit the signal from each electrode are also noticeable in the picture. Of note, than only two wires are needed for data acquisition.

The prototype device obtained with the considered fabrication process is shown in FIG. 21. During fabrication and/or surface mounting on the test structure, micro-fractures were accidentally generated in the thin and brittle metallization layers. Such micro-fractures may cause interruption of electrical continuity within an electrode. To prevent this, a preliminary re-metallization step was conducted, whereby the existing substrate metallization was completely etched away and replaced by slightly thicker layers of Copper and Nickel. Such layers were added on both sides of the PVDF film through sputter deposition before the preparation step described above. Upon completion of the fabrication process, lack of electrical continuity was still detected at a few locations. This was easily fixed by applying patches of conductive glue, as seen in FIG. 21. It is believed that this issue can be eliminated in the future by refining the metallization thickness and/or composition.

Signal Processing

Figure 22:
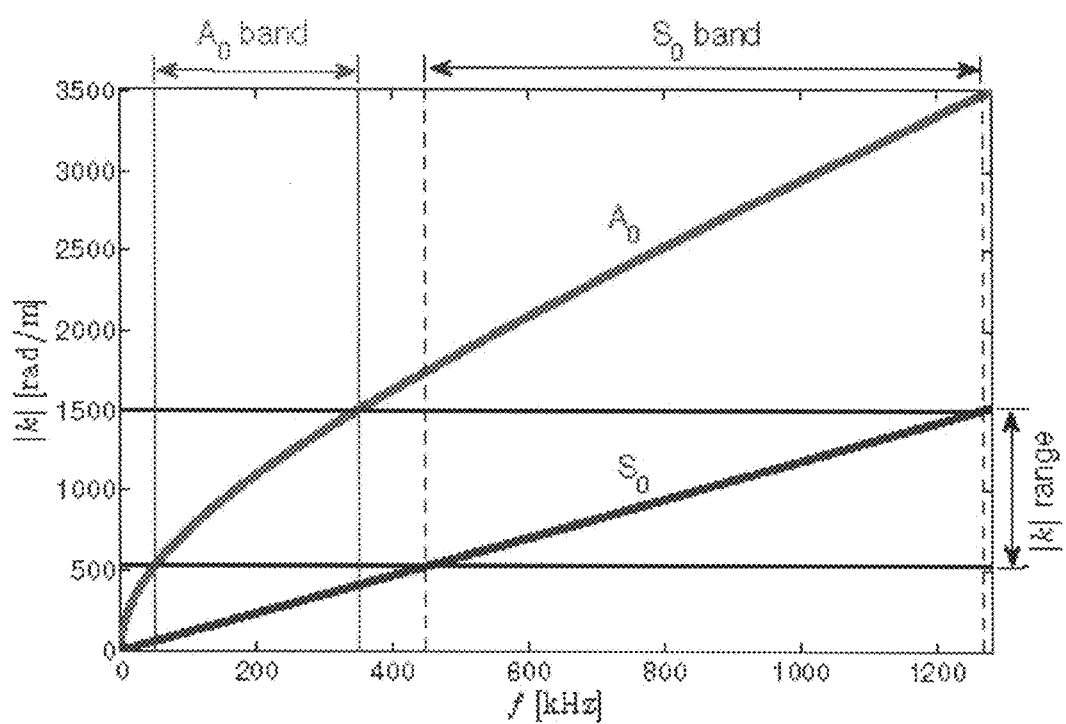
FIG. 22: Dispersion curves for 0.75-mm-thick aluminum, with indication of the active bands for A0- and S0-based directional filtering with the fabricated FSATs.

Sensing performance of the fabricated WS-FSAT is evaluated in terms of its ability to localize single and multiple acoustic sources in various pitch-catch configurations. In each configuration, GWs are generated by one or more broadband sources, which are assumed to excite as uniformly as possible the whole frequency range spanned by the directional filtering of the spiral sensor. The active band is set by the wavenumber involved in WS-FSAT design through dispersion curves of the waveguide under test. For 0.75-mm-thick aluminum, the k interval associated with the fabricated device (see TABLE 7 and FIG. 20(c)) corresponds to decoupled frequency bands for the fundamental A0 and S0 modes, as illustrated in FIG. 22. A0-based imaging is considered in this work for practicality, which corresponds to an active band in the [50, 350] kHz range, as specified in TABLE 7.

Figure 23:
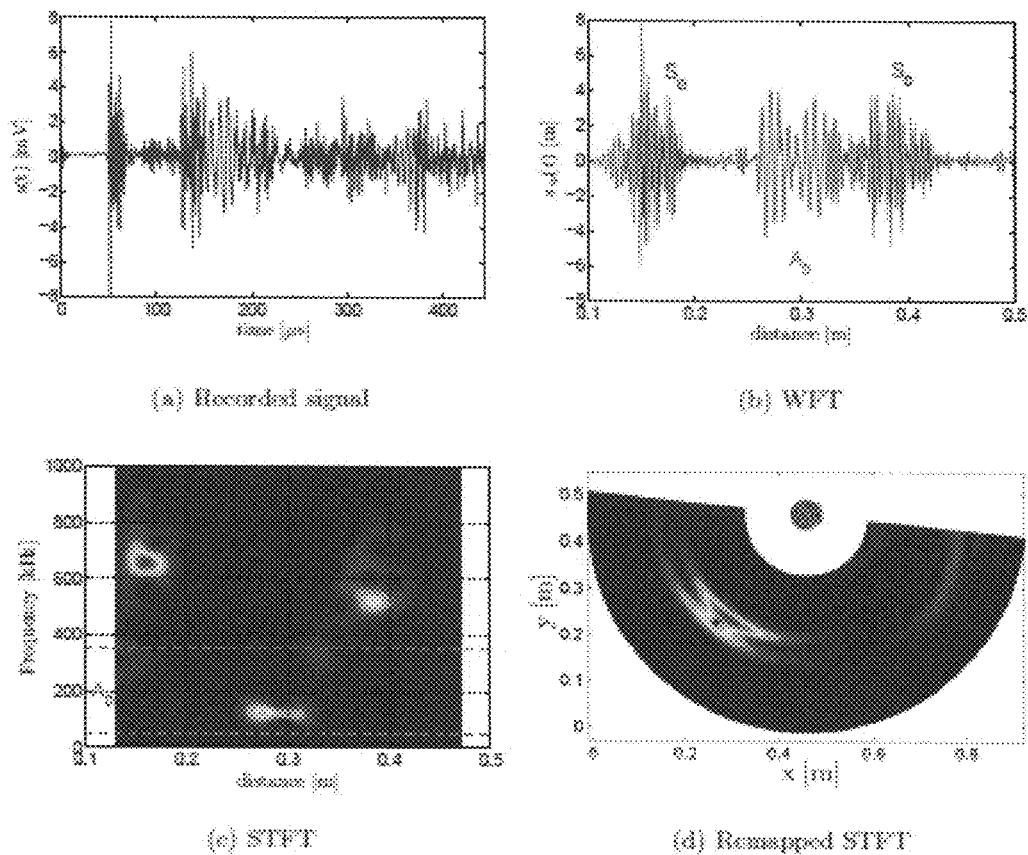
FIG. 23: Spectrogram remapping based imaging approach. (a) WS-FSAT output signal. (b) Warped signal: A0 wave packet is highlighted. (c) Spectrogram of the warped signal with indication of the original (unwarped) frequencies on the y axis. The active A0 band for the considered WS-FSAT is also highlighted. (d) Imaging results after frequency-direction mapping and polar to Cartesian coordinate conversion. Actual location of the acoustic source is indicated by the '+' marker.

Localization of relevant acoustic events is obtained by processing the WS-FSAT output signal with a spectrogram remapping approach. This technique involves dispersion compensation for the selected GW mode through frequency warping, followed by a coordinate remapping which directly converts a time-frequency representation of the warped signal into an image of the monitored waveguide region. The procedure is schematically summarized in FIG. 23 with reference to an experimental signal recorded by the prototype WS-FSAT in a single source configuration.

FIGS. 23(a) and 23(b) show the recorded time waveform (differential signal between WS-FSAT electrodes) and its Warped Frequency Transform (WFT), respectively. The WFT basically acts as a non-uniform Fourier Transform (NUFT) followed by a uniform IFT. The NUFT step is characterized by a deformation of the frequency axis through a warping map, which is designed to counteract the frequency-wavenumber non-linearity introduced by dispersion for a specific propagating mode.

As a consequence, the warped waveform can be equivalently plotted as a function of the distance traveled by the tracked mode, as shown in FIG. 23(b). The warping map used to produce the signal in this FIG. is tailored to A0, thus removing dispersion from the associated wave packets and mapping them to the correct range distance, while dispersion of S0 components is generally increased and their position has no physical meaning. The warped A0 wave packet associated with the first arrival of the acoustic source signal is highlighted in FIG. 23(b) and has approximately the same size as the WS-FSAT diameter, while other contributions correspond to S0 incident and reflected components.

Although this may not be immediately evident from direct inspection of the warped signal, it is clearly revealed by its Short Time Fourier Transform (STFT) displayed in FIG. 23(c) after a first remapping step meant to unwarp the frequency axis. Only the wave packet highlighted in FIG. 23(b) has a frequency content which is compatible with the active A0 band marked by dashed lines in FIG. 23(c), while the spectral composition of remaining contributions identifies them as S0 components according to the associated active band indicated in FIG. 22.

Each frequency within the relevant A0 range corresponds to a specific direction of arrival through the characteristic frequency-angle map of the spiral sensor. The warped spectrogram portion highlighted in FIG. 23(c) can thus be straightforwardly converted into a polar image of the inspected area. A final conversion to Cartesian coordinates provides imaging results in FIG. 23(d), where the acoustic source is correctly localized. The distance information can be further remapped to properly account for the actual signal path in scatterer imaging applications.

It is worth noting that S0 components are automatically discarded with the presented approach thanks to the decoupling effect produced by the sensor. Upon sufficient broadband excitation of the waveguide, however, these contributions might be fruitfully exploited to improve localization confidence and imaging capabilities of the proposed SHM apparatus.

Experimental Validation

Setup

Figure 24:
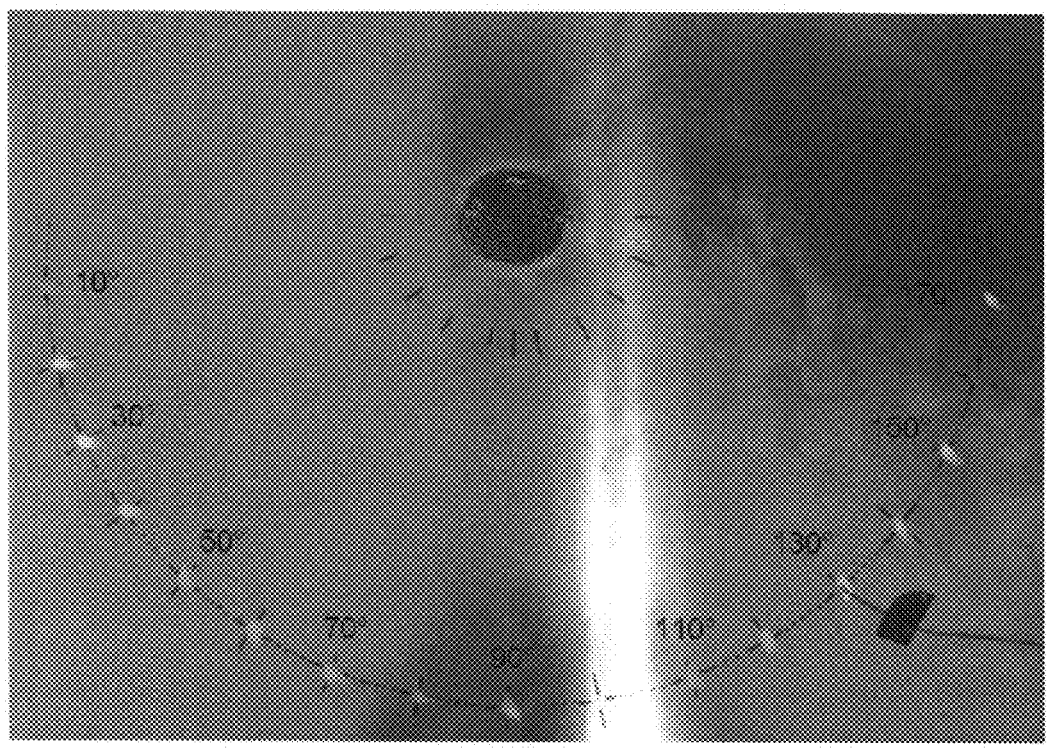
FIG. 24: Experimental Setup used to test the fabricated WS-FSAT.

The experimental setups used to test the prototype device is shown in FIG. 24. The sensor is attached to a 0.75-mm-thick 6061 aluminum plate of size 915 mm×915 mm through a thin epoxi layer. 5-mm-diameter PZT transducers are used as acoustic sources for testing as they are found to provide relatively uniform excitation within the active bandwidth of the WS-FSAT when driven by a Panametrics-NDT 5058PR broadband pulser with 900 V output voltage and 10%-90% rise time of 40 ns. An angular grid with 10° resolution and fixed radial distance of 300 mm from the spiral center is considered, as can be seen from FIG. 24. PZTs are bonded to the plate through Sonotech shear-couplant gel so that they can be easily detached and moved to different locations without leaving unused transducers acting as scatterers on the plate. WS-FSAT response is recorded by a Tektronix TDS2024 oscilloscope controlled via GPIB by a Matlab graphical user interface (GUI), which allows storing and processing the acquired signal for imaging purpose. Each acquisition is averaged 128 times to reduce measurement noise.

Single Source Imaging

Functionality of the WS-FSAT prototype is initially verified by sequentially activating a single acoustic source. PZT actuator discs are bonded to the plate to act as GW sources at each of the 17 positions indicated in FIG. 24. Each of the actuators is fired individually and the differential signal received between the two WS-FSAT electrodes is recorded and processed. The WS-FSAT filtering capabilities are first evaluated through the spectrum of the signal portion within a window of width approximately equal to 150 mm, centered on the first arriving A0 wave packet generated by the active source. Resulting FT amplitudes associated with the 20°, 70°, 110°, and 170° sources are shown in FIG. 25 along with the expected peak frequency depending on the direction of arrival of the incoming wave.

Figure 25:
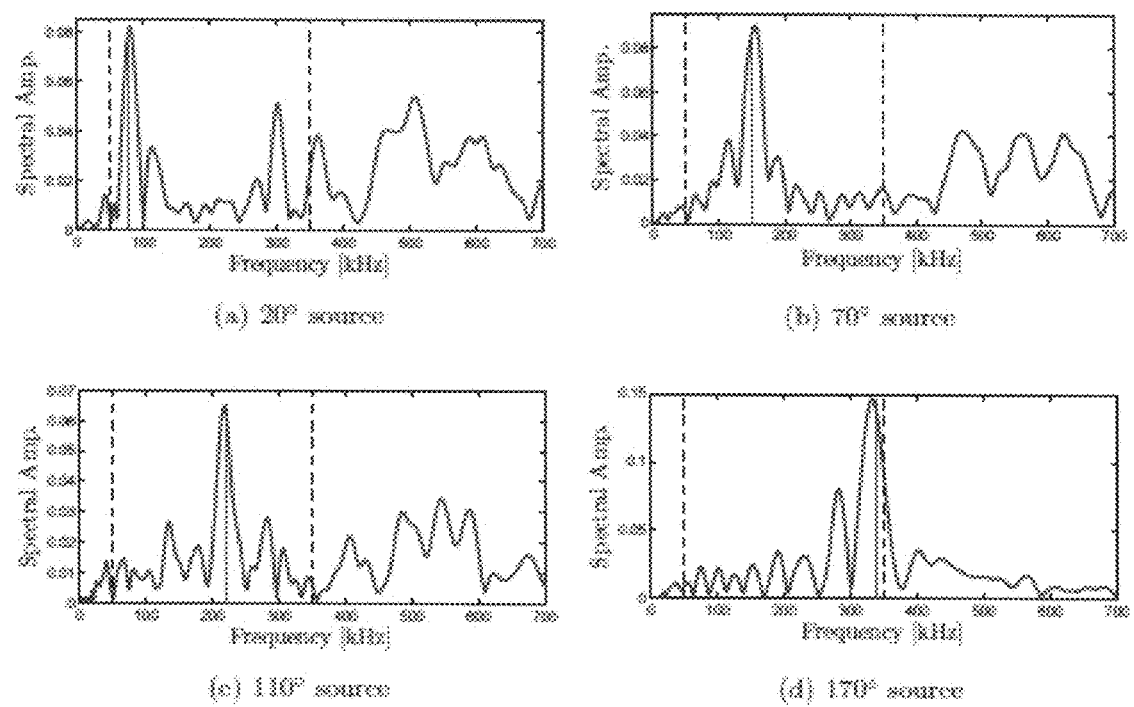
FIG. 25: FFT amplitude of the wave packet associated with a PZT source at the (a) 20°, (b) 70°, (c) 110°, and (d) 170° location in FIG. 24. Solid and dashed vertical lines indicate the expected peak frequency and boundaries of the active sensor bandwidth, respectively.
Figure 26:
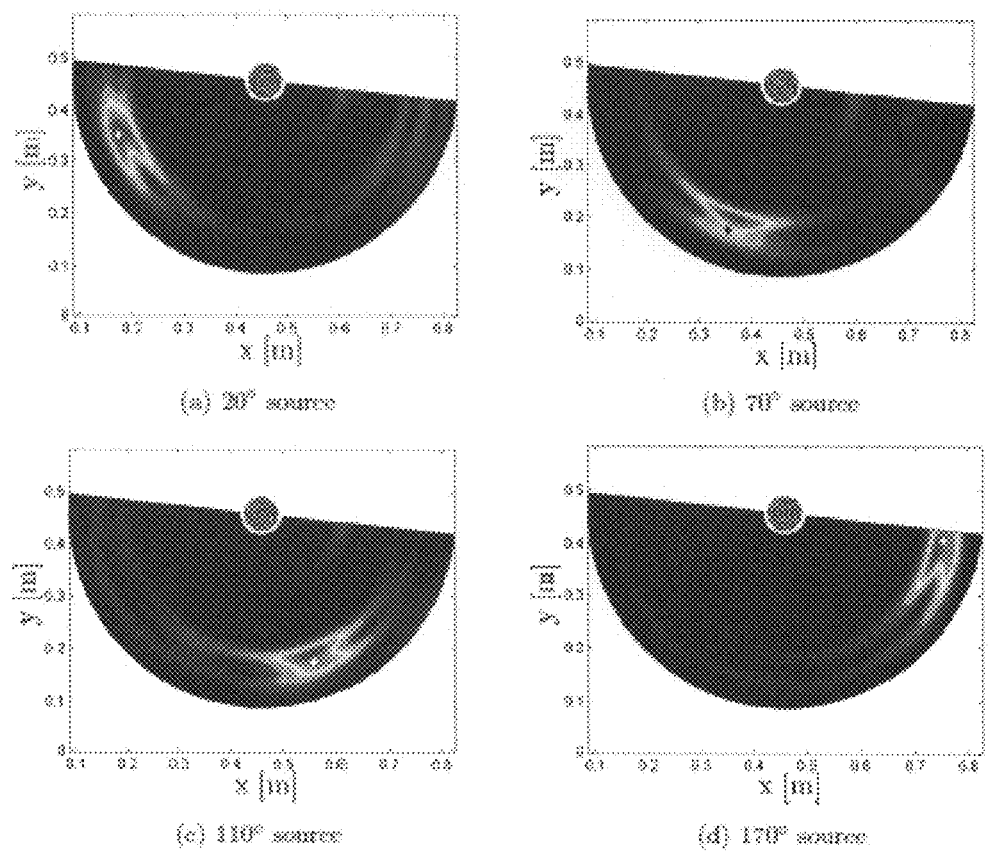
FIG. 26: Imaging of PZT sources at the (a) 20°, (b) 70°, (c) 110°, and (d) 170° location in FIG. 24. '+' markers indicate the actual source position.

Boundaries of the active device bandwidth for A0-based sensing are indicated by dashed lines in FIG. 25. These results and similar ones found for the other directions of arrival demonstrate the excellent filtering performance of the prototype WS-FSAT, which provides consistently good imaging accuracy as shown in FIG. 26. Double energy spots associated with each source location in this FIG. are due to the characteristic two-peak wave packets generated by dual-polarity WS-FSAT because of their particular shape. Full [0°, 180°] scanning capabilities of the sensor are apparent from FIG. 26. The slight inclination of imaged half-planes is simply due to a small positioning error during surface-mounting of the device, which was properly accounted for during signal processing.

Multiple Source Imaging

Figure 27:
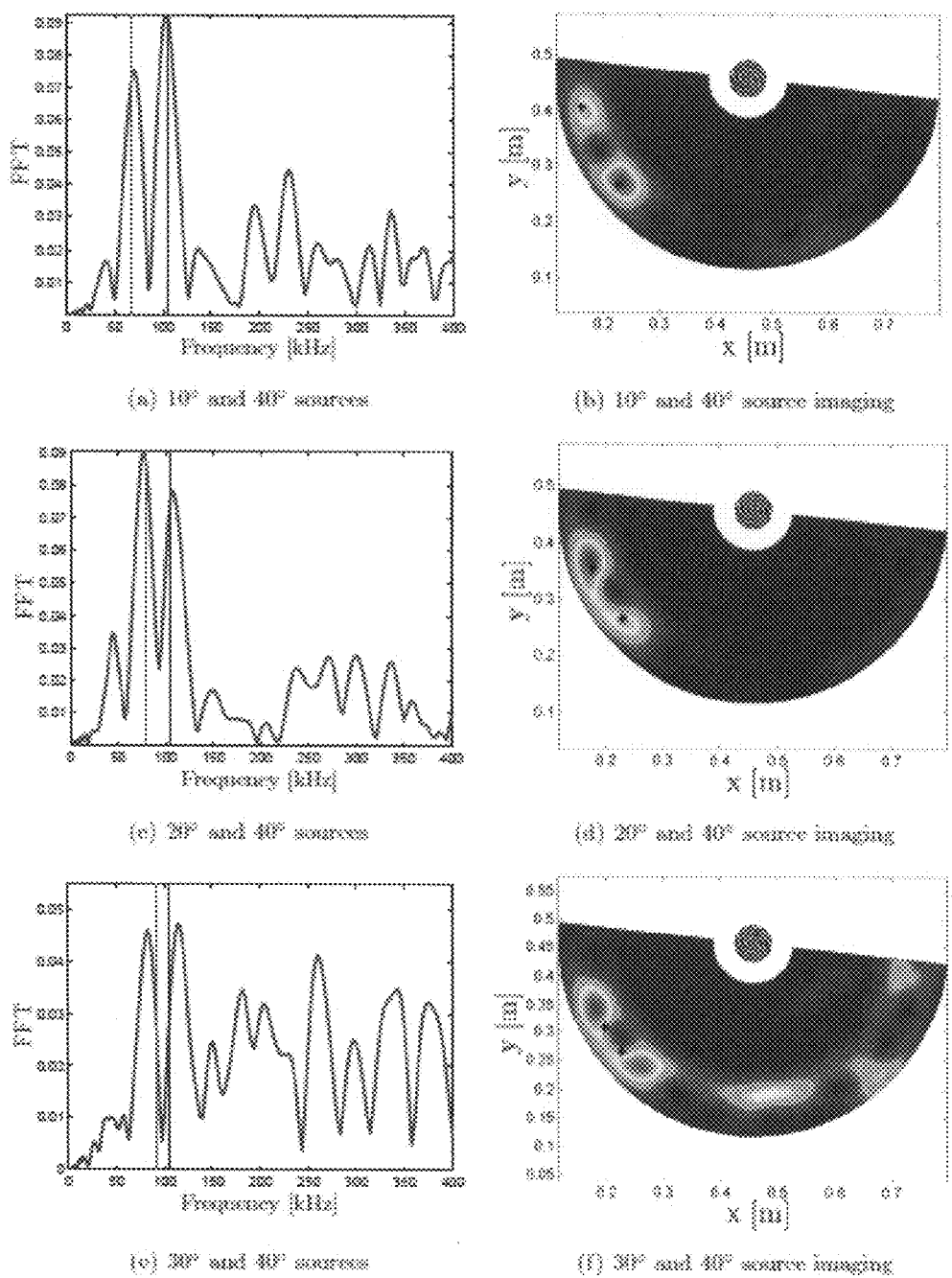
FIG. 27: (a), (c), (e) FFT of sensor output and (b), (d), (f) imaging results for double source excitation. Indicated angular positions of the acoustic sources correspond to locations illustrated in FIG. 24. Expected peak positions are indicated by vertical lines in (a), (c), (e), while actual PZT locations are marked by '+' symbols in (b), (d), (0.

Angular resolution of the dual-polarity WS-FSAT is also evaluated in the presence of two simultaneously activated acoustic sources. FIG. 27 shows results of this test in the case where one source is fixed at the 40° location in FIG. 24 and a second PZT is in turn activated at the 10°, 20° and 30° positions.

Two distinct peaks are clearly visible in the spectrum of the recorded signals in FIGS. 27(a), (c), (e), although peak spacing is slightly larger than expected in the 10° separation case of FIG. 27(e) and spurious contributions appear. Imaging results are excellent for acoustic sources with 30° and 20° separation, as shown in FIGS. 27(b) and (d), respectively. Acoustic sources with 10° angular spacing and radial distance of 300 mm from WS-FSAT center can still be clearly distinguished, as demonstrated by FIG. 27(f), but imaging results are less accurate and more noisy in this case. This effect, however, is not necessarily due to the small source separation. In fact, the degradation observed in FIG. 27(f) is suspected to be partially or entirely caused by accidental factors, the most important of which is scarce repeatability of the PZT bonding using a shear couplant.

The employed gel is not conductive and 5-mm diameter PZTs do not have dual contact pads on the top surface, which means that electric connections should be realized on both sides of the wafers to properly excite the transducers. In the tests described herein, the aluminum plate itself is used as ground contact, assuming that the bonding gel layer is sufficiently thin. Based on that, a suitable amount of couplant gel must therefore be used when bonding each PZT to provide the right trade-off between effective shear coupling to the plate and the achievement of sufficient excitation voltage. This process, however, is hardly repeatable, and coupling differences are particularly problematic when two PZTs are simultaneously excited, and they generate different amplitude waves. In addition, the performance of each PZT source varies over time. All of the differences in PZT coupling with the plate make the analysis of two sources data more challenging, since each source generates signals of different strengths, which may reduce the localization capabilities of the WS-FSAT. The coupling effciency, and repeatability, along with ways to improve them are the object of current testing. These uncertainty causes might be also responsible for the increased noise level in FIGS. 27(e) and (f), as suggested by better results found in other 10° separation configurations at different directions, although a limited number of angular locations could be tested due to the highlighted measurement difficulties. Overall, however, the results in FIG. 27 show the effectiveness of the WS-FSAT in the presence of multiple sources, even when in close proximity of each other. This is a distinctive feature of the considered concept and the associated signal processing scheme, which does not operate solely based on time-of-flight information, and therefore is not effected by the presence of multiple scattering events, and cross-scattering among the multiple sources.

As shown, the present invention comprises the design, fabrication and testing of Frequency Steerable Acoustic Transducers (FSAT). The considered configuration corresponds to the quantized shape associated with a spiral in wavenumber space. The shape provides the transducer with frequency-dependent directionality, which is here exploited for the localization of acoustic broadband sources. This is achieved with limited hardware complexity, and a simple signal processing strategy.

Combining the frequency-angular mapping provided by the transducer shape and a dispersion removal process based on frequency warping, allows for the localization of acoustic sources in a plate structure. Prototype WS-FSATs are fabricated by patterning the electrodes' geometry on both sides of a metallized PVDF substrate. The process involves photolithographic techniques conventionally used in microfabrication processes.

Tests of a dual-electrode, 65-mm-diameter transducer demonstrate its excellent sensing performance over the [0°, 180°] angular range, where single and multiple sources can be effectively localized.

Various functionality, such as that described above with respect to the controllers and analyzers can be implemented in hardware and/or software. In this regard, a computing device can be used to implement this functionality in some embodiments.

In terms of hardware architecture, such a computing device can include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set) or generally any device for executing software instructions.

The memory can include any one or combination of volatile memory elements (e.g., random access memory (RAM, such as DRAM, SRAM, SDRAM, VRAM, etc.)) and/or nonvolatile memory elements (e.g., ROM, hard drive, tape, CD-ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the computing device is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

One should note that the flowcharts included herein show the architecture, functionality, and operation of a possible implementation of software. In this regard, each block can be interpreted to represent a module, segment, or portion of code, which comprises one or more executable instructions for implementing the specified logical function(s). It should also be noted that in some alternative implementations, the functions noted in the blocks may occur out of the order and/or not at all. For example, two blocks shown in succession may in fact be executed substantially concurrently or the blocks may sometimes be executed in the reverse order, depending upon the functionality involved.

One should note that any of the functionality described herein can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" contains, stores, communicates, propagates and/or transports the program for use by or in connection with the instruction execution system, apparatus, or device. The computer readable medium can be, for example but not limited to, an electronic, magnetic, optical, electromagnetic, infrared, or semiconductor system, apparatus, or device. More specific examples (a nonexhaustive list) of a computer-readable medium include a portable computer diskette (magnetic), a random access memory (RAM) (electronic), a read-only memory (ROM) (electronic), an erasable programmable read-only memory (EPROM or Flash memory) (electronic), and a portable compact disc read-only memory (CDROM) (optical).

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A spiral array system for performing structural health monitoring of a component comprising:
   spiral-shaped array components;
   the array components being selectively operative in an actuator mode and a sensor mode such that:
   in the actuator mode, simultaneous activation of the array components produces waves with frequency dependent directional characteristics that propagate through the component; and
   in the sensor mode, the array components detect waves propagated through the component and filter frequency content of the waves on the basis of direction of propagation of the waves;
   a controller operative, in the actuator mode, to provide a control signal to the array components; and
   a single channel communicatively coupling the controller and the array components such that the array components produce frequency dependent directional waves responsive to the control signal provided via the single channel and the simultaneous activation of the array components.

* * * * *